(12) United States Patent
Keller

(10) Patent No.: US 7,479,498 B2
(45) Date of Patent: *Jan. 20, 2009

(54) TREATMENTS FOR VIRAL INFECTIONS

(75) Inventor: Robert H. Keller, Hollywood, FL (US)

(73) Assignee: Phoenix Biosciences, Inc., Hollywood, FL (US)

( * ) Notice: Subject to any disclaimer, the term of this patent is extended or adjusted under 35 U.S.C. 154(b) by 14 days.

This patent is subject to a terminal disclaimer.

(21) Appl. No.: 11/353,467

(22) Filed: Feb. 14, 2006

(65) Prior Publication Data

US 2006/0241059 A1 Oct. 26, 2006

Related U.S. Application Data

(63) Continuation-in-part of application No. 11/177,038, filed on Jul. 8, 2005, which is a continuation-in-part of application No. 10/745,060, filed on Dec. 22, 2003, which is a continuation of application No. 09/644,414, filed on Aug. 23, 2000, now Pat. No. 6,734,192.

(60) Provisional application No. 60/150,261, filed on Aug. 23, 1999.

(51) Int. Cl.
*A61K 31/47* (2006.01)
*A61K 31/277* (2006.01)

(52) U.S. Cl. .................. 514/311; 514/299; 514/183; 546/134

(58) Field of Classification Search ................ 514/311, 514/299, 183; 546/134
See application file for complete search history.

(56) References Cited

U.S. PATENT DOCUMENTS

| 4,800,081 A * | 1/1989 | Albrecht et al. ............. 424/607 |
| 6,262,019 B1 | 7/2001 | Keller et al. |
| 6,399,654 B1 * | 6/2002 | Lin et al. .................... 514/456 |

FOREIGN PATENT DOCUMENTS

| DE | 3812595 A | 10/1988 |
| WO | WO 94/20108 | 9/1994 |
| WO | WO 01/13907 | 3/2001 |

OTHER PUBLICATIONS

Sperber et al. (AIDS Research and Human Retroviruses (1993), 9(1), 91-98) (Abstract Sent).*
Muller et al. (Progress in molecular and subcellular biology, (1996) vol. 16, pp. 44-57) (Abstract Sent).*
Fawzi et al. (Lancet, (May 16, 1998) vol. 351, No. 9114, pp. 1477-1482) (Abstract Sent).*
Al-Harthi et al. (Journal of Infectious diseases (1997), 176 (5), pp. 1175-1179) (Abstract Sent).*

* cited by examiner

*Primary Examiner*—Shaojia Anna Jiang
*Assistant Examiner*—Michael C Henry
(74) *Attorney, Agent, or Firm*—Frommer Lawrence & Haug, LLP; Ronald R. Santucci

(57) ABSTRACT

The present invention relates to improved methods and compositions for treating viral infections and other diseases and conditions that induce a cytokine storm. More particularly, the present invention relates to novel compositions comprising quercitin, and an anti-convulsant, such as phenytoin, in combination with mulivitamins as an anti-viral composition and methods of use thereof.

4 Claims, 5 Drawing Sheets

TREATMENTS FOR VIRAL INFECTIONS

CROSS-REFERENCE TO RELATED APPLICATIONS

This application is a continuation-in-part of U.S. application Ser. No. 11/177,038, filed on Jul. 8, 2005, which is a continuation-in-part of U.S. application Ser. No. 10/745,060, filed on Dec. 22, 2003, which is a continuation of U.S. application Ser. No. 09/644,414, filed on Aug. 23, 2000, now issued as U.S. Pat. No. 6,734,192 and claiming priority from U.S. Provisional Application Ser. No. 60/150,261, filed on Aug. 23, 1999. This application also makes reference to U.S. Pat. No. 6,262,019, filed on Apr. 29, 1999.

Each of these applications, patents, and each document cited in this text, and each of the documents cited in each of these applications, patents, and documents ("application cited documents"), and each document referenced or cited in the application cited documents, either in the text or during the prosecution of the applications and patents thereof, as well as all arguments in support of patentability advanced during prosecution thereof, are hereby incorporated herein by reference.

FIELD OF THE INVENTION

The present invention relates to improved methods and compositions for treating viral infections. More particularly, the present invention relates to novel compositions comprising quercitin, and an anti-convulsant, such as phenytoin, in combination with multivitamins as an anti-viral composition and methods of use thereof.

BACKGROUND OF THE INVENTION

The present invention relates to improved methods and compositions for treating viral infections including retroviruses and hepadnaviruses, such as HIV and Hepatitis C, in infected subjects.

The disease now known as acquired immunodeficiency syndrome (AIDS) was first recognized as early as 1979. The number of cases reported to the Centers for Disease Control and Prevention (CDC) has increased dramatically each year since then, and in 1982, the CDC declared AIDS a new epidemic. It has been estimated that over 40 million people have been diagnosed with AIDS.

Retroviruses were proposed as the causative agent of AIDS, with human immunodeficiency virus type 1 (HIV-1) emerging as a preferred name for the virus responsible for progression to AIDS. Antibodies to HIV are present in over 80% of subjects diagnosed as having AIDS or pre-AIDS syndrome, and it has also been found with high frequency in identified AIDS risk groups.

AIDS is characterized by a compromised immune system attributed to the systemic depletion of $CD4^+$ T-lymphocytes (T-cells), as well as the unresponsiveness and incompetence of remaining $CD4^+$T-cells in the immune system. The level of $CD4^+$ T-cells serves as a diagnostic indicator of disease progression. HIV infected $CD4^+$ T-cells are known to be directly cytopathic to other $CD4^+$ T-cells and this single cell-killing event is initiated via interactions between the HIV envelope protein (gp120/41) interaction and the CD4 receptor molecule on host cells. Highly virulent isolates of HIV induce syncytia (defined as >4 nuclei within a common cell membrane), a process associated with rapid loss of $CD4^+$ T-cells and disease progression.

HIV infection in humans causes general immunosuppression and can involve other disorders, such as blindness, myelopathy, and dementing neurological disorders, such as, for example, the AIDS dementia complex, a common and important cause of morbidity in subjects in advanced stages of infection. HIV infection has been documented in various areas of the CNS, including the cerebral cortex, spinal cord, and retina. Price et al. (1988, Science 239:586) and Ho et al. (1989, Annals in Internal Medicine 111:400) review the clinical, epidemiological, and pathological aspects of the AIDS dementia complex, and suggest that the mechanism underlying the neurological dysfunction may be indirect tissue damage by either viral- or cellular-derived toxic substances released by infected cells.

There is considerable difficulty in diagnosing the risk of development of AIDS. AIDS is known to eventually develop in almost all of individuals infected with HIV. A subject is generally diagnosed as having AIDS when a previously healthy adult with an intact immune system acquires impaired T-cell immunity. The impaired immunity usually appears over a period of 18 months to 3 years. As a result of this impaired immunity, the subject becomes susceptible to opportunistic infections, various types of cancers, such as Kaposi's sarcoma, non-Hodgkins lymphoma, and other disorders associated with reduced functioning of the immune system.

HIV replicates through a DNA intermediate. Each virus particle contains two identical, single-stranded RNA molecules surrounded by the viral nucleocapsid protein. The remaining core of the virus is composed of the capsid and matrix proteins. Enzymes required for replication and integration of the viral genetic materials into the host cells are also contained within the capsid. The outer coat of the virus particle comprises viral envelope glycoproteins and membrane derived from the host cell.

No sufficiently effective treatment capable of preventing progression to AIDS is available, although HAART (highly active anti-retroviral therapy) has reversed some of the immunodeficiency caused by AIDS. Essentially, all subjects with opportunistic infections and approximately half of all subjects with Kaposi's sarcoma have died within two years of diagnosis. Attempts at reviving the immune system in subjects with AIDS have so far been substantially unsuccessful.

While 3'-azido-3'-deoxythymidine (AZT) has been most often used in treating HIV infection and AIDS, it has considerable negative side effects, such as reversible bone marrow toxicity, and the development of viral resistance to AZT by the subject. Thus, other methods of treatment are highly desirable.

Influenza virus, like HIV, is an enveloped single stranded RNA virus. Influenza viruses belong to the Orthomyxoviridae family of viruses. There are three serotypes of influenza viruses: A, B and C. Influenza A occurs the most frequently and is also the more virulent form, being responsible for the majority of influenza epidemics and pandemics. Influenza A can be further subtyped based on the surface antigens H (hemagglutinin—the protein responsible for binding of the influenza virus to host cells) and N (neuraminidase), which are the major antigenic determinants. Influenza strains can also be classified based on geographical location of the first isolate, serial number and year of isolation.

In recent years, outbreaks of the highly pathogenic H5N1 strain of avian influenza (a type of Influenza A) species have caused major concern. In 1997 an outbreak of H5N1 in Hong Komg spread rapidly through poultry and as a result millions of poultry were culled. The H5N1 virus has continued to spread, resulting in poultry outbreaks throughout Asia and also, more recently, in Russia, Romania, and Turkey. Of particular concern is the fact that the H5N1 virus can cross the species barrier. There have now been several cases of direct transmission of the virus from poultry to humans, resulting in almost a 50% mortality rate among those humans infected. H5N1 infects epithelial cells and causes an unbridled pro-inflammatory immune response inducing a so-called "cytokine storm". The induction of this cytokine storm is one the major causes of pathogenicity as it leads to death of epithelia cells, acute respiratory distress syndrome and, in many cases death. There is concern that the H5N1 virus may evolve through antigenic drift to generate a form capable of human-to-human transmission. Thus, there is much concern about the possibility of a future human pandemic which could result in millions of deaths worldwide.

The neuraminidase inhibitor Oseltamivir (Tamiflu™) is the main current treatment option for avian influenza, and stockpiling of this drug is part of pandemic preparation plans in the U.S. and elsewhere. However, Tamiflu™-resistant H5N1 variants were recently isolated from two patients who died from the infection (de Jong et al., New England Journal of Medicine, Volume 353, December 2005, p 2667-2672). Therefore, there is a need in the art for the development of new treatments capable of treating and/or ameliorating the effects of avian influenza infection in subjects, including human and avian subjects.

Viruses traditionally do not respond to antibiotic therapy. Therefore, other treatments are preferred when treating viral infections. One such therapy revolves around the use of protease inhibitors to disrupt the viral replication cycle. Protease inhibitor therapy has the potential to be used in the treatment of a wide range of diseases, including viral infections, such as those caused by retroviruses (e.g., HIV), hepadnaviruses (e.g., hepatitis C virus) herpesviruses (e.g., herpes simplex virus and cytomegalovirus) and myxoviruses (e.g., influenza virus), as well as parasitic protozoa (e.g., *Cryptosporidium* and *Plasmodium*), in cancer chemotherapy and various pathological disorders. However, the protease inhibitors used in HAART have resulted in significant complications including lipodystrophy, hepatic failure and coronary artery disease. Accordingly, it would be a highly desirable advance in the art to provide improved compositions and methods for the treatment of viral infections that do not display the undesirable side effects associated with known antiviral treatments.

The inventors of the present application believe that the novel compositions disclosed herein are useful in treating and/or ameliorating the effects of infection with HIV and the H5N1 strain of avian influenza. The compositions of the invention may also be useful in the treatment of viral infections caused by other single stranded RNA viruses and in the treatment of other diseases and medical conditions that induce a "cytokine storm".

SUMMARY OF THE INVENTION

The present invention relates to novel compositions comprised of therapeutically effective amounts of quercetin or one of its derivatives, an anticonvulsant component, such as phenytoin, with at least one calcium channel blocker component (or metabolites thereof), a quinoline component, quinoline-quinone component or intermediates or derivatives such as chloroquine, in combination with a multivitamin component. The components combine and interact in a manner to effectively treat viruses by reducing viral activity in infected subjects.

Accordingly, one aspect of the present invention provides an antiviral composition comprising quercetin or one of its derivatives, at least one calcium channel blocker component, an anticonvulsant component, a quinoline component or derivatives thereof, and a multivitamin component in sufficient amounts to treat and reduce viral activity in an infected subject.

In another embodiment, the weight ratio of the calcium channel blocker component to the quinoline component to the anticonvulsant component is about 100-240 mg to about 200-250 mg to about 100-300 mg.

The anticonvulsant component can comprise phenytoin or derivatives thereof. The quinoline component comprises at least one member selected from the group consisting of chloroquine, mefloquine, mefloquine hydrochloride, primaquine, primaquine phosphate, carboxyprimaquine and derivatives thereof.

The calcium channel blocker component comprises at least one member selected from the group consisting of verapamil, nimodipine, diproteverine, SmithKline drug no. 9512, isoptin, nitrendipine, diltiazam, mioflazine, flunarizine, bepridil, lidoflazine, CERM-196, R-58735, R-56865, ranolazine, nisoldipine, nicardipine, PNZ00-110, felodipine, amlodipine, R-(+)-202-791, R-(+) Bay K-8644, and derivatives thereof.

The multivitamin component can comprise β-carotene, N-acetylcysteine, glucosamine, Vitamin C, Vitamin D, Vitamin E, calcium, magnesium, boron, zinc, and chromium piconolate.

In one embodiment, the components are in particle form and tableted with pharmaceutically acceptable carriers or tableting agents. In another embodiment, the components are in combination with a pharmaceutically acceptable liquid carrier. Further, the composition can comprise about 100 to 240 mg calcium channel blocker component and about 200 to 250 mg quinoline component.

Another aspect of the present invention provides a method of reducing viral activity in an infected subject, comprising administering to the subject a therapeutically effective amount of a composition comprising quercetin or one of its derivatives, at least one calcium channel blocker, an anticonvulsant, a quinoline or derivatives thereof, and multivitamins, in sufficient amounts to treat and reduce viral activity in the subject.

In another aspect, a method of reducing viral activity in an infected subject is provided, comprising administering to the subject a therapeutically effective amount of the composition of the invention. In one preferred aspect, the invention provides methods of reducing viral activity in subjects infected with an enveloped single-stranded RNA virus, wherein the methods comprise administering to the subject a therapeutically effective amount of the composition of the invention. In another preferred, the invention provides methods of reducing immune activation and inflammation in subjects suffering from a medical condition or disease that induces a cytokine storm, wherein the methods comprise administering to the subject a therapeutically effective amount of the composition of the invention. In further preferred embodiments the invention provides methods of reducing HIV activity in an HIV-infected subject comprising administering to the subject a therapeutically effective amount of the composition of the invention. In other preferred embodiments the invention provides methods of reducing activity of the H5N1 avian influenza virus in infected subjects comprising to the subject a therapeutically effective amount of the composition of the invention.

In other aspects, the compositions of the present invention are administered in combination with the compositions described in U.S. Pat. No. 6,262,019, the contents of which are incorporated herein by reference. The compositions described in U.S. Pat. No. 6,262,019 elevate the glutathione concentration in cells, and can be beneficially administered to patients infected with various viral infections, such as HIV or avian influenza, including the H5N1 strain of avian influenza.

Another aspect of the present invention provides a method of increasing glutathione levels in a virally-infected subject, comprising administering to the subject a therapeutically effective amount of a composition comprising quercetin or one of its derivatives, at least one calcium channel blocker component, an anticonvulsant component, a quinoline component or derivatives thereof, and a multivitamin component, in sufficient amounts to increase glutathione levels in the subject. The quercetin, calcium channel blocker, anticonvulsant component and quinoline work synergistically with the multivitamin component to increase glutathione levels. The anticonvulsant (such as dilantin or phenytoin) along with the calcium channel blocker component (such as verapamil) "calms" the immune system by decreasing calcium influx leading to a decrease in Jak and Stat phosphorylation, thus decreasing cell activation. The multivitamin component synergizes with this, for example by increasing glutathione and DHEA levels, which in turn decreases oxidative stress, decreases interleukin 1 (IL1), interleukin 6 (IL6) and tumor necrosis factor alpha (TNF alpha) production which decreases viral activity.

In another aspect, a method of increasing glutathione levels in a virally infected subject is provided, comprising administering to the subject a therapeutically effective amount of the composition of the present invention in conjunction with a the multivitamin component.

These and other embodiments are disclosed or are obvious from and encompassed by, the following Detailed Description.

BRIEF DESCRIPTION OF THE DRAWINGS

The following Detailed Description, given by way of example, but not intended to limit the invention to specific embodiments described, may be understood in conjunction with the accompanying Figures, incorporated herein by reference, in which.

DETAILED DESCRIPTION OF THE INVENTION

Figure 1:
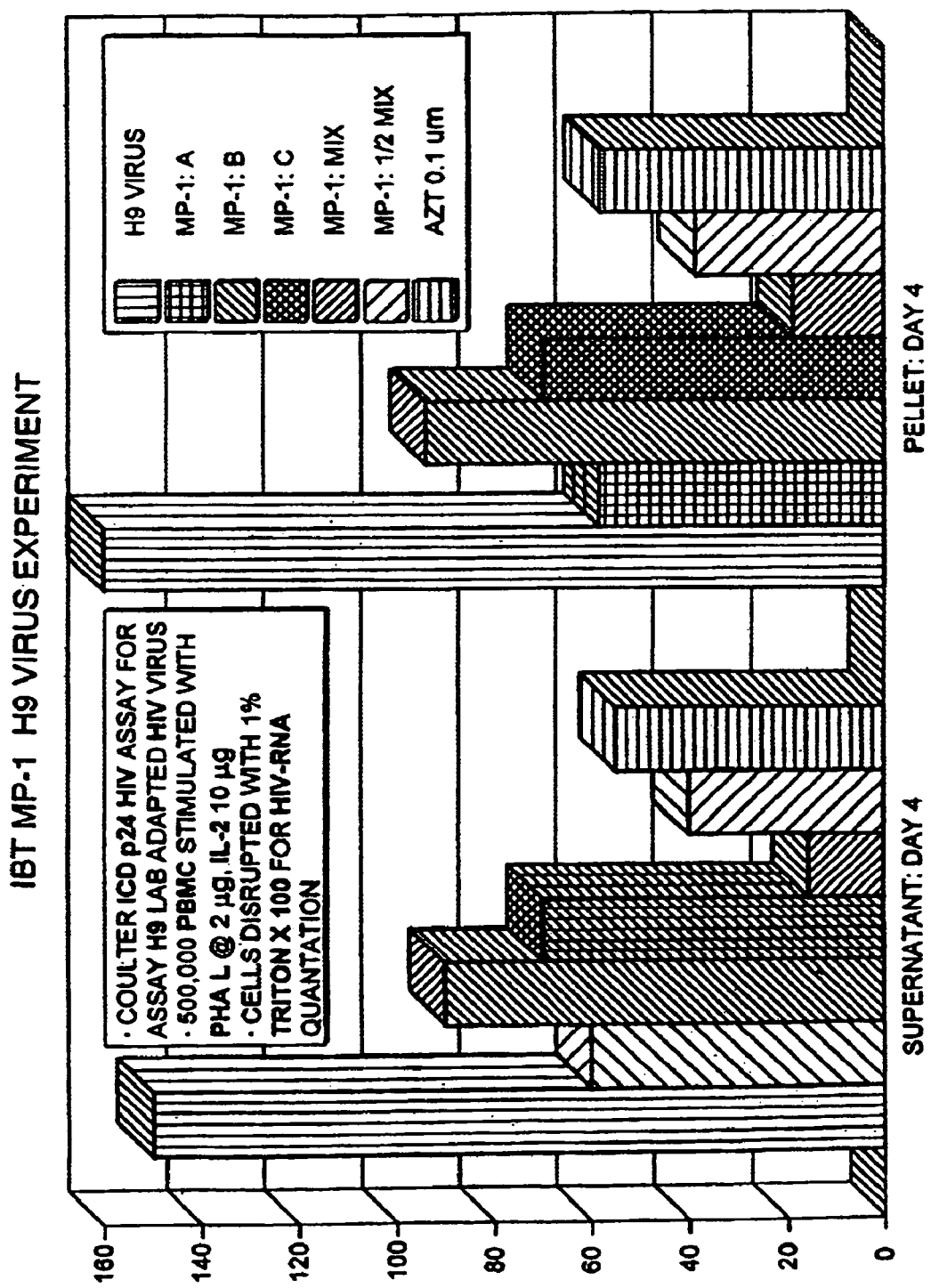
FIG. 1 is a graph depicting the results from 100 experiments on the effects of a composition in accordance with the invention on the viral load (measured by $p24^{gag}$ ICD) of peripheral blood lymphocytes infected with a laboratory adapted HIV virus (H9)

In this disclosure, "comprises," "comprising," "containing" and "having" and the like can have the meaning ascribed to them in U.S. Patent law and can mean "includes," "including," and the like; "consisting essentially of" or "consists essentially" likewise has the meaning ascribed in U.S. Patent law and the term is open-ended, allowing for the presence of more than that which is recited so long as basic or novel characteristics of that which is recited is not changed by the presence of more than that which is recited, but excludes prior art embodiments.

A "subject" in the context of the present invention can be a vertebrate, such as a mammal; more advantageously a human, or a companion or domesticated or food-producing or feed-producing or livestock or game or racing or sport or laboratory animal such as murines, primates, bovines, canines, felines, caprines, ovines, porcines, or equines. In addition a "subject" in the context of the present invention can be avian subject, such as for example a poultry species. As used herein, the term "poultry" refers to those avians typically raised for meat or egg production, such as chickens, turkeys, ducks, or geese. Preferably, the subject is a human. An "infected subject" is a subject who has suffers from a viral infection or has otherwise been infected with a virus. A similar term used in the context of the present invention is "virally-infected subject".

It has been surprisingly demonstrated that compositions comprising quercetin or one of its derivatives, anticonvulsants, such as phenytoin, with calcium channel blockers (or metabolites thereof), quinoline, quinoline-quinone or intermediates or derivatives such as chloroquine in combination with multivitamins, can be therapeutically effective in treating viral infection. The present invention also provides methods of decreasing viral activity and methods of increasing glutathione levels using the inventive compositions when administered to a subject in need thereof.

The compositions and methods of the present invention can advantageously be used to inhibit viral diseases, such as, but not limited to HIV, herpes simplex virus 1 (HSV1), herpes simples virus 2 (HSV2), varicella zoster virus (herpes zoster), variola virus, hepatitis virus A, B, and C, cytomegalovirus, Epstein Barr, papilloma virus, viral influenza including avian influenza, in particular the highly virulent H5N1 strain of avian influenza, viral parainfluenza, adenovirus, viral encephalitis, viral menigitis, arbovirus, arenavirus, picomavirus, coronavirus, and syncytial viruses, among many other viral species. In addition, the compositions and methods of the invention could be used to treat parasitic diseases, such as for example, Malaria which is caused by protozoan parasites of the genus *Plasmodium* (including *Plasmodium falciparum, Plasmodium vivax, Plasmodium ovale* and *Plasmodium malaria*.

The present invention described herein demonstrates that multivitamins, when administered in combination with quercetin or one of its derivatives, an anticonvulsant such as phenytoin, a calcium channel blocker such as verapamil, and a quinoline, quinoline-quinone or intermediates or derivatives, can slow the progression of HIV to AIDS (Fawzi, W. W. et al, (2004) N. Engl. J. Med. 351: 23-32). Furthermore, decreased glutathione, present in a significant percentage of subjects afflicted with HIV, is an independent predictor of death in HIV. Glutathione (GSH) is a prevalent antioxidant in humans and reduces oxidative stress in HIV (Herzenberg, L.

A. et al, (1997) Proc. Natl. Acad. Sci. USA 94: 1967-1972). The compositions and methods of the present invention substantially halt or prevent the depletion of glutathione, thereby improving the quality of life and delaying viral progression in virally-infected subjects.

The compositions of the present invention can also be used in the treatment or amelioration of other viral infections, such as avian influenza infection, and other infections caused by single stranded RNA viruses. Furthermore, the compositions of the present invention can also be used to reduce immune activation and a "cytokine storm", such as may be induced by a variety of other diseases and in a variety of disease states. For example, the compositions and methods of the present invention substantially reduce the inflammatory response in cells treated with a surrogate for the highly pathogenic H5N1 strain of avian influenza.

The term "cytokine storm" is well known in the art and refers to the an excessively vigorous inflammatory response characterized by excessive production of pro-inflammatory cytokines such as interferons, interleukins, and tumor necrosis factors. The induction of a cytokine storm is a known characteristic of infection with the avian influenza strain H5N1 (see, for example, Wong et al. "Avian influenza virus infections in humans" Chest; January 2006; Volume 129(1), pages 156-68, and Yuen et al. "Human infection by avian influenza A H5N1" Hong Kong Med Journal. June 2005, Volume 11(3), pages 189-99). In fact, the cytokine storm is believed to be one of the reasons for the severe symptoms and even mortality caused by H5N1 infection.

In addition, the induction of a cytokine storm has been reported in many other diseases, including diseases caused by pathogenic agents such as viruses and bacteria, autoimmune diseases, and cancer. (See, for example, Link et al. "The cytokine storm in multiple sclerosis", Mult Scler. 1998 February; 4(1):12-5; Makhija et al. "Cytokine storm in acute pancreatitis" J. Hepatobiliary Pancreat Surg. 2002; 9(4):401-10; Faulkner et al. "The mechanism of superantigen-mediated toxic shock: not a simple Th1 cytokine storm". J Immunol. 2005 Nov. 15; 175(10):6870-7). Furthermore, the occurrence of a cytokine storm has been noted following organ transplantation and other types of surgery (see, for example, Aikawa, N. "Cytokine storm in the pathogenesis of multiple organ dysfunction syndrome associated with surgical insults" Nippon Geka Gakkai Zasshi 97(9):771-777, 1996. The compositions of the present invention can be useful in the treatment of all such diseases and medical conditions characterized by an induction of a cytokine storm.

The term "low glutathione levels" as used herein means a blood glutathione level below about 440 μg glutathione/$10^{10}$ erythrocytes, as determined by the colorimetric method of Beutler et al. (Improved Method for the Determination of Blood Glutathione, (1963) J. Lab. Clin. Med., 61: 882-8). Normal levels in humans can range from about 440 to about 654 μg/$10^{10}$ erythrocytes.

The inclusion of anticonvulsants, such as phenytoin (also known in the art as Dilantin) into compositions comprising a calcium channel blocker, a quinoline, quinoline-quinone or derivative thereof, and optionally, quercetin, can result in decreased Vitamin A and Vitamin C absorption (Tuchweber, B. et al, (1976) 100(2): 100-5). Multivitamins, such as vitamins A and C, are important antioxidants that improve the function of phenytoin as an antiviral agent (Dubick, M. A. and Keen, C. L. (1985) J. Nutr. 115(11): 1481-7). Additionally, quercetin promotes the conversion of β-carotene, present in the compositions of the present invention, to Vitamin A (Gomboeva, S. B. et al, (1998) Biochemistry (Moscow) 63(2): 185-90), which also improves the function of phenytoin.

Anti-convulsants such as phenytoin, mephenytoin and ethotoin can be advantageously used in the compositions and methods of the present invention. While phenytoin is described herein, any anticonvulsant can be used in the compositions and methods of the invention.

Phenytoin sodium is a known antiepileptic compound. Phenytoin, phenytoin sodium, and procedures for their manufacture are well-known, see for example U.S. Pat. No. 4,696,814, issued Sep. 29, 1987; U.S. Pat. No. 4,642,316, issued Feb. 10, 1987; and U.S. Pat. No. 2,409,754, issued Oct. 22, 1946, the contents of which are incorporated herein by reference. Phenytoin is the generic name for 5,5-diphenyl-2,4-imidazolidinedione. It also is known as diphenylhydantoin. It is used extensively to treat convulsive disorders such as epilepsy. Because phenytoin is poorly soluble in aqueous mixtures, it cannot be effectively used in injectable solutions, or even in solid preparations for oral use. The compound generally is utilized as a sodium salt, which is readily soluble in water.

Phenytoin sodium is commercially available as an oral extended release pharmaceutical composition. Phenytoin sodium is well known and is also referred to in the art as the monosodium salt of 5,5-diphenyl hydantoinate (phenytoin). Phenytoin sodium is commercially available in several polymorphic forms. In the context of the present invention, phenytoin sodium incorporated into the current invention can be any of the polymorphic mixtures commercially available. Any salt of phenytoin can be used in the context of the present invention; the term "derivative(s) thereof" refers to any phenytoin salt, hydrochlorides, malates, tartrates, maleates, succinates, chelates, among many other forms.

Phenytoin salts are water-soluble whereas phenytoin is water insoluble. The solubility difference between phenytoin salts and phenytoin is an important factor when preparing pharmaceutical preparations because solubility will influence or dictate the types and amounts of other ingredients to be used in the pharmaceutical preparation. Phenytoin sodium is highly water-soluble. With regard to dosage levels, the anticonvulsant must be present in an amount corresponding to the generally recommended adult human dosages for a particular anticonvulsant. Specific dosage levels for the anticonvulsants that can be used herein as given, inter alia, in the "Physicians' Desk Reference", 1996 Edition (Medical Economics Data Production Company, Montvale, N.J.) as well as in other reference works including Goodman and Gilman's "The Pharmaceutical Basis of Therapeutics" and "Remington's Pharmaceutical Sciences". Given the wide variation in dosage level of the anticonvulsant, which depends to a large extent on the specific anticonvulsant being administered, there can similarly be a wide variation in the dosage level of calcium channel blocker component, quinoline component, multivitamin component, and quercetin component or derivatives thereof t added to the composition so as to provide an antiviral effect. These amounts can be determined for a particular drug combination in accordance with this invention employing routine experimental testing.

While the anticonvulsant component, calcium channel blocker component, quinoline component, multivitamin component, and quercetin component, or derivatives thereof need not be administered together, they must both be present in the subject at effective levels at the same time. While it is within the scope of the invention to separately administer the anticonvulsant component, the calcium channel blocker component, the quinoline component or derivatives thereof, the multivitamin component, and the quercetin component or derivatives thereof, as a matter of convenience, it is preferred that these components be co-administered in a single dosage form.

The multivitamins can serve as a catalyst, activator, phytochemical initiator, nutritional supplement, and auxiliary carrier. The multivitamin component can comprise one or more of the following: a water soluble vitamin, a fat soluble vitamin, vitamin A, vitamin B complex, (B vitamin complex), vitamin C, vitamin D, vitamin E, vitamin K, vitamin B1, vitamin B2, vitamin B5, vitamin B6, vitamin B12, vitamin B15, niacinamide, folacin, folic acid, dehydroepiandrosterone (DHEA), β-carotene, N-acetylcysteine, glucosamine, N-acetyl-D-glucosamine, sylimarin, biotin, para-aminobenzoic acid (PABA), betaine, α-lipoic acid, calcium, copper, magnesium, manganese, selenium (i.e., selenomethionine), zinc, boron, and chromium piconolate, but are not limited to these examples. Preferably, the multivitamin component comprises at least β-carotene, Vitamin C, Vitamin D, Vitamin E, N-acetylcysteine, glucosamine, N-acetyl-D-glucosamine, calcium, magnesium, boron, zinc, and chromium piconolate. Transition and alkaline earth metals such as calcium can be administered as the carbonate, citrate, ascorbate, pantothenate, phosphate, or chloride salt. Similarly, zinc and magnesium can be administered as a carbonate, glycinate, phosphate, piconolate, or chloride salt. It is well within the purview of the skilled artisan to determine which vitamins are particularly suitable for inclusion into the compositions of the present invention, without undue experimentation.

One preferred embodiment of the multivitamin component described herein is "Immune Vitality", a tablet formulation comprising multivitamins in the following amounts. The compositions of the present invention can comprise administering Immune Vitality, wherein Immune Vitality tablets can be added to the compositions described herein or taken simultaneously with the calcium channel blocker component, quinoline component, anticonvulsant component and optionally, quercetin component. Preferably, the multivitamin component, which can be Immune Vitality, is administered in the amount of four capsules per administration of the antiviral compositions of the invention.

TABLE 1

Components of Immune Vitality

| Component | Amounts |
| --- | --- |
| β-carotene | 12500 IU |
| Vitamin C (calcium ascorbate) | 1000 mg |
| Vitamin D | 400 IU |
| Vitamin E succinate | 400 IU |
| Vitamin B1 | 50 mg |
| Vitamin B2 | 50 mg |
| Vitamin B6 | 50 mg |
| Vitamin B12 | 50 mcg |
| Niacinamide | 50 mg |
| Folic Acid | 400 mcg |
| Biotin | 100 mcg |
| Magnesium glycinate | 500 mg |
| Zinc picolinate | 50 mg |
| Selenomethionine | 200 mcg |
| Copper glycinate | 2500 mcg |
| Manganese citrate | 500 mcg |
| Molybdenum amino acid chelate | 500 mcg |
| D-calcium pantothenate | 25 mg |
| p-aminobenzoic acid (PABA) | 25 mg |
| Boron citrate | 8 mg |
| Betaine | 25 mg |
| N-acetylcysteine | 500 mg |
| N-acetyl-D-glucosamine | 250 mg |
| Dehydroepiandrosterone (DHEA) | 25 mg |
| α-lipoic acid | 150 mg |

TABLE 1-continued

Components of Immune Vitality

| Component | Amounts |
| --- | --- |
| Chromium picolinate | 200 mcg |
| Calcium citrate | 1000 mg |

It has been determined that calcium channel blockers can have a positive treatment effect on AIDS infected subjects. The in vitro effect of calcium channel blockers on HIV infection both in HIV adapted cell lines (HUT/H9) as well as acutely infected peripheral blood lymphocytes were studied. In aggregate, these experiments revealed a 50-60% reduction in HIV production (by detection of HIV RNA by polymerase chain reaction) and ICD p24$^{gag}$ antigen at pharmacologically achievable concentrations.

These results are supported by other research on calcium channel blockers. Inhibition of calcium ($Ca^{2+}$) influx during cell activation by blocking voltage regulated $Ca^{2+}$ channels can result in decreased symptoms in subjects suffering from hyperactive immune systems. It has also been demonstrated that voltage regulated $Ca^{2+}$ channel blockade significantly reduces debilitating symptoms in chronic fatigue and immune deficiency syndrome (CFIDS). In addition, there was a concordant decrease in T-cell activation without any change in immune effect or mechanisms (i.e., natural killer cell cytotoxicity, IgG levels). This decreased activation involves decreased interleukin synthesis and decreased mitogen reactivity.

The addition of quinolines, such as quinoline-quinones, or intermediates thereof, such as chloroquine, has demonstrated synergistic effects when combined with calcium channel blockers, multivitamins, and anticonvulsants, as provided in the compositions of the present invention. Chloroquine and its analogues, including hydroxychloroquine, have been shown to inhibit a variety of viral infections, as well as reduce immune reactivity. Both effects are mediated by a change in intracellular pH, which inhibits viral, as well as cellular enzymes involved in activation. Hydroxychloroquine (HCQ), an antimalarial agent, can be used to treat subjects with autoimmune disease, and can suppress human immunodeficiency virus (HIV) replication in vitro in T-cells and monocytes by inhibiting post-transcriptional modification of the virus.

Chloroquine is a drug of choice for treating acute malaria caused by quinoline-sensitive strains. Chloroquine kills merozoites, thereby reducing parasitemia, but does not affect the hypnozoites of *Plasmodium vivax* and *Plasmodium ovale* in the liver. These are killed by primaquine, which can be used in malaria treatment to prevent relapses. Chloroquine, which can be administered in solid or liquid form, combined with known pharmaceutically effective carriers, is a synthetic 4-aminoquinoline typically formulated as the phosphate salt for oral use and as the hydrochloride for parenteral use. The salts, hydrochlorides, tartrates, maleates, malates, succinates, chelates and other forms of the active ingredients described herein are encompassed by the term "derivatives". Thus, compositions in accordance with the invention can include chloroquine and derivatives thereof.

Chloroquine is rapidly and almost completely absorbed from the gastrointestinal tract, reaches maximum plasma concentrations (50-65%) protein-bound in about 3 hours, and is rapidly distributed to the tissues. Because it is concentrated in the tissues, it has a very large apparent volume of distribution of about 13,000 L. From these sites, it is slowly released and metabolized. The drug readily crosses the placenta. It is excreted in the urine with a half-life of 3-5 days. Renal excretion is increased by acidification of the urine.

Because of its very large volume of distribution, a loading dose should be given when an effective schizonticidal plasma level of chloroquine is urgently needed in the treatment of acute attacks. To avoid life-threatening toxicity when chloroquine is given parenterally, it should be provided by slow intravenous infusion or by small incremental doses intramuscularly. A therapeutically effective plasma concentration appears to be approximately 30 μg/L against sensitive *P. falciparum* and 15 μg/L against *P. vivax*.

Chloroquine is rapidly and completely absorbed following oral administration. Usually 4 days of therapy suffice to cure the disease. The drug concentrates in erythrocytes, liver, spleen, kidney, and lung as well as leukocytes. Thus, it has a very large volume of distribution. It persists in erythrocytes. The drug also penetrates into the central nervous system and traverses the placenta. Chloroquine is dealkylated by the hepatic mixed function oxidases, but some metabolic products retain anti-malarial activity. Both parent drug and metabolites are excreted predominantly in the urine. Excretion rate is enhanced as urine is acidified.

Chloroquine is a highly effective blood schizonticide and is the 4-aminoquinoline drug that is most widely used in chemoprophylaxis and in treatment of attacks by *P. vivax*, *P. ovale*, and other species of malaria-causing agents. Chloroquine is not active against the preerythocytic *Plasmodium* and does not eradicate *P. vivax* or *P. ovale* infections because it does not eliminate the persisting liver stages of those parasites.

The exact mechanism of antimalarial action has not been determined. Chloroquine may act by blocking the enzymatic synthesis of DNA and RNA in both mammalian and protozoal cells and forming a complex with DNA that prevents replication or transcript to RNA. Within the parasite, the drug concentrates in vacuoles and raises the pH of these organelles, interfering with the parasite's ability to metabolize and utilize erythrocyte hemoglobin. The drug may also decrease DNA synthesis in the parasite by disrupting the tertiary structure of the nucleic acid. Interference with phospholipid metabolism within the parasite has also been proposed. Selective toxicity for malarial parasites depends on a chloroquine-concentrating mechanism in parasitized cells. Chloroquine's concentration in normal erythrocytes is 10-20 times that in plasma; in parasitized erythrocytes, its concentration is about 25 times that in normal erythrocytes.

Subjects usually tolerate chloroquine well when it is used for malaria prophylaxis (including prolonged use) or treatment. Gastrointestinal symptoms, mild headache, pruritus, anorexia, malaise, blurring of vision, and urticaria are not uncommon. Taking the drug after meals may reduce some adverse effects. Rare reactions include hemolysis in glucose-6-phosphate dehydrogenase (G6PD)-deficient persons, impaired hearing, confusion, psychosis, convulsions, blood dyscrasias, skin reactions, alopecia, bleaching of hair, and hypotension.

Chloroquine is contraindicated in subjects with a history of liver damage, alcoholism, or neurologic or hematologic disorders. Certain antacids and anti-diarrheal agents (kaolin, calcium carbonate, and magnesium trisilicate) can interfere with the absorption of chloroquine and should not be taken within about 4 hours before or after chloroquine administration.

Quinine, a bitter-tasting alkaloid, is rapidly absorbed, reaches peak plasma levels in 1-3 hours, and is widely distributed in body tissues. Approximately 80% of plasma quinine is protein-bound; red blood cell levels are about 20% of the plasma level and cerebrospinal fluid concentrations about 7%. The elimination half-life of quinine is 7-12 hours in normal persons but 8-21 hours in malaria-infected persons in proportion to the severity of the disease. Approximately 80% of the drug is metabolized in the liver and excreted for the most part in the urine. Excretion is accelerated in acid urine.

With constant daily doses, plasma concentrations usually reach a plateau on the third day. In normal or in mild infection, standard oral doses result in plasma levels of about 7 μg/mL; in severe malaria, higher plasma levels are reached. A mean plasma concentration of over about 5 μg/mL is effective to eliminate asexual parasites of *P. vivax* malaria and a somewhat higher concentration in *P. falciparum* malaria. Concentrations lower than 2 μg/mL have little effect, whereas concentrations over 7 μg/mL are generally accompanied by adverse reactions of "cinchonism." Because of this narrow therapeutic range of about 2-7 μg/mL, adverse reactions are common during quinine treatment of *P. falciparum* malaria.

Quinine is a rapidly acting, highly effective blood schizonticide against the four malaria parasites. The drug is gametocidal for *P. vivax* and *P. ovale*, but not very effective against *P. falciparum* gametocytes. Quinine has no effect on sporozoites or the liver stages of any of the parasites. The drug's molecular mechanism is unclear. Quinine is known to depress many enzyme systems. It also forms a hydrogen-bonded complex with double-stranded DNA that inhibits strand separation, transcription, and protein synthesis.

Mefloquine is used in prophylaxis and treatment of chloroquine-resistant and multidrug-resistant *P. falciparum* malaria. It is also effective in prophylaxis against *P. vivax* and presumably against *P. ovale* and *P. malaria*. Mefloquine hydrochloride is a synthetic 4-quinoline methanol derivative chemically related to quinine. It is generally only given orally because intense local irritation can occur with parenteral use. It is well absorbed, and peak plasma concentrations are reached in 7-24 hours. A single oral dose of 250 mg of the salt results in a plasma concentration of 290-340 ng/mL, whereas continuation of this dose daily results in mean steady state plasma concentrations of 560-1250 ng/mL. Plasma levels of 200-300 ng/mL may be necessary to achieve chemo-suppression in *P. falciparum* infections. The drug is highly bound to plasma proteins, concentrated in red blood cells, and extensively distributed to the tissues, including the central nervous system. Mefloquine is cleared in the liver. Its acid metabolites are slowly excreted, mainly in the feces. Its elimination half-life, which varies from 13 days to 33 days, tends to be shortened in subjects with acute malaria. The drug can be detected in the blood for months after dosing ceases.

Primaquine phosphate is a synthetic 8-aminoquinoline derivative. After oral administration, the drug is usually well absorbed, reaching peak plasma levels in 1-2 hours, and then is almost completely metabolized and excreted in the urine. Primaquine's plasma half-life is 3-8 hours and its peak serum concentration is 50-66 ng/mL; trace amounts to the tissues, but only a small amount is bound there. Its major metabolite is a deaminated derivative, carboxyprimaquine, that reaches plasma concentrations more than ten times greater than those of the parent compound, is eliminated slowly (half-life 22-30 hours), and accumulates with daily dosing; peak serum concentrations after 14 daily doses are 432-1240 ng/mL. Whether primaquine or one of its metabolites is the active compound has not been determined. The mechanism of primaquine's antimalarial action is not well understood. The quinoline-quinone intermediates derived from primaquine are electron-carrying redox compounds that can act as oxidants. These intermediates are thought to produce most of the hemolysis and methemoglobinemia associated with primaquine's use.

Quercetin [2-(3,4-Dihydroxyphenyl)-3,5,7-trihydroxy-4H-1-benzopyran-4-one] and derivatives thereof is a natural flavonoid and is used for its ability to eliminate toxic compounds found in the liver. It has anti-hepatotoxic, antiviral, anti-inflammatory and antibacterial properties. Quercetin can be synthesized by the method of Shakhova, I. K. et al., (1962) Zh. Obsheh. Khim. 32: 390, incorporated by reference. Quercetin can inhibit binding of HIV to CD4 receptors on host cells, as well as inhibition of both viral integrase and viral reverse transcriptase, and has also been shown to inhibit HIV activity. Example 8 of the present application provides data demonstrating the ability of compositions comprising quercetin to bind to CD4+ T cells in HIV-infected patients. It is believed that the efficacy of the compositions of the present invention against other viral diseases, such as against avian influenza and in particular the H5N1 strain of avian influenza, may be mediated, at least in part, by the binding of quercetin to the surface of cells thereby preventing viruses from binding to these cells. For example, it is believed that the compositions of the present invention comprising quercetin may also bind to/block epithelial cells thereby blocking binding of avian influenza viruses. It is also believed that the compositions of the present invention comprising quercetin may have antiviral effects against other viral diseases by binding to/blocking the cells usually infected by that virus. For example, it is believed that binding/blocking of hepatocytes by quercitin may block or inhibit binding of Hepatitis C virus.

Quercetin is a naturally occurring flavone, often found in plant material that is consumed by animals, including humans, on a daily basis. Quercetin, a common constituent of plants, was identified from a traditional Chinese medicine (TCM) extract that was determined to be an aryl hydrocarbon (Ah) receptor antagonist. The chemical configuration of quercetin, like flavones generally, is composed of two benzene rings linked through a heterocyclic pyrine ring. Quercetin has been shown to be a genotoxic compound that can initiate carcinogenic activity in certain tissues if administered at high dosages over a prolonged period (Dunnick, J. K., and Hailey, J. R. (1992), Fundam. Appl. Toxicol. 19(3): 423-31). It has been demonstrated that when in the presence of transformed cancer cells, quercetin has an anti-proliferative effect on those transformed, cancerous cells. (Scambia, G. et al., (1993) Int. J. Cancer 54(3): 462-6).

Phenytoin has been reported to decrease levels of dehydroepiandrosterone (DHEA) (Levesque, L. A. et al, (1986) J. Clin. Endocrinol. Metab. 63(1): 243-5) and GSH (Ono, H. et al, (2000) Clin. Chim. Acta 298(1-2): 135-43), resulting in a heightened cortisol/DHEA ratio in epileptic subjects (Ono, H. et al, (2000) Clin. Chim. Acta 298(1-2): 135-43; Gallagher, E. P. and Sheehy, K. M., (2001) Toxicology Sciences 59: 118-126), which is associated with increased lipodystrophy, even in the absence of anti-retroviral therapy (ART) (Shevitz, A. et al, (2001) AIDS 15(15): 1917-30; Kotler, D. P. (2003) AIDS Read. 13(4 Suppl): S5-9). Decreased DHEA levels have also been reported to decrease the quality of life in advanced HIV (Piketty, C. et al, (2001) Clin. Endocrinol. (Oxford) 55(3): 325-30). A decrease in DHEA is further associated with decreased CD4 levels (de la Torre, B. et al, (1997) Clin. Exp. Rheumatol. 15(1): 87-90) and increased HIV viral loads (Christeff, N. et al, (1999) Nutrition 15(7-8): 534-9). Increased HIV activity associated with decreased DHEA has been related to an increase in interleukin-6 (IL-6) production (Centurelli, M. A. and Abate, M. A. (1997) Ann. Pharmacother. 31(5): 639-42) and a decrease in IL-2 production, a hallmark of HIV/AIDS progression (Ferrando, S. J. et al., (1999) J. Acquir. Immune Defic. Syndr. 22(2): 146-54; Yang, J. Y. et al, (1993) AIDS Res. Hum. Retroviruses 9(8): 747-54). Increases in IL-6 production subsequently increase HIV activity as well an increase in levels of the pro-inflammatory cytokines IL-1 and tumor necrosis factor-α (TNFα), which permits reactivation of latent HIV in cells. Without wishing to be bound by any one theory, it is believed that the present composition and methods described herein decrease IL-1, TNFα, and IL-6 secretion and impedes the upregulation of the long terminal repeat reporter gene required for activation of latent HIV (Christeff, N. et al, (2000) Ann. NY Acad. Sci. 917: 962-70). Elevated cortisol/DHEA ratio is also associated with weight loss in HIV (Christeff, N. et al, (1997) Psychoneuroendocrinology 22 Suppl. 1: S11-18; Ono, H. et al, (2000) Clin. Chim. Acta 298(1-2): 135-43).

In addition, the use of phenytoin decreases the absorption of $Zn^{2+}$, $Cu^{2+}$ and $Mg^{2+}$ and the production of reduced glutathione (Wells, P. G., et al, (1997) Mutat. Res. 396(1-2): 65-78). The reduction in GSH production can be also reversed by quercetin, which increases GSH production by 50% (Myhrstad, M. C. et al, (2002) 32(5): 386-93) by stimulating downstream events that promote GSH production (Fiorani, M. et al, (2001) Free Radic. Res. 34(6): 639-48). Reduced glutathione has been reported to be an independent predictor of death in late stage HIV/AIDS subjects (Herzenberg, L. A. et al, (1997) Proc. Natl. Acad. Sci. USA 94: 1967-1972). The reasons for this are manifold, but include a decrease in GSH levels, ultimately resulting in increased oxidative stress in HIV. An object of the present invention provides a method of increasing glutathione levels in virally infected subjects, comprising administering a therapeutically effective amount of the compositions of the present invention.

Oxidative stress can be exacerbated by the decrease in Vitamin A, C and DHEA in subjects taking phenytoin (Dubick, M. A. and Keen, C. L. (1985) J. Nutr. 115(11): 1481-7; Ono, H. et al, (2000) Clin. Chim. Acta 298(1-2): 135-43). It also results in greater non-HIV infected $CD4^+$ T-cell apoptosis (Fiorani, M. et al, (2001) Free Radic. Res. 34(6): 639-48). Apoptosis of $CD4^+$ cells are also decreased by quercetin that is protected from oxidation by vitamin C (Vrijsen, R. et al, (1988) J. Gen. Virol. 69: 1749-51). The importance of decreasing the accelerated apoptosis reported in HIV has been demonstrated in the art, which describe that corticosteroids decrease apoptosis and increase CD4 counts in HIV without a significant increase in HIV viral activity (Yang, J. Y. et al, (1993) AIDS Res. Hum. Retroviruses 9(8): 747-54; Christeff, N. et al, (2000) Ann. NY Acad. Sci. 917: 962-70).

In addition, the presence of multivitamins, such as N-acetylcysteine, glucosamine and Vitamin C protect quercetin from oxidation and improves its anti-HIV function by increased production of GSH (Myhrstad, M. C. et al, (2002) Free Radic. Bio. Med. 32(5): 396-93; Jan, C. Y. et al, (1991) Biochim. Biophys. Acta 1086(1): 7-14). GSH also reduces the teratogenicity associated with phenytoin administration (Wells, P. G. et al, (1997) Mutat. Re. 396(1-2): 65-78) and prevents phenytoin from becoming a free radical induced by the hepatic cytochrome P450 system (Jan, C. Y. et al, (1991) Biochim. Biophys. Acta 1086(1): 7-14). This can reduce the accelerated metabolism of many drugs by phenytoin by decreasing phenytoin's increased activation of the hepatic cytochrome P450 system. In addition, glutathione (GSH) restores the electrophysiologic impairment of neuromuscular function associated with phenytoin (Raya, A. et al, (1995) Free Radic. Biol. Med. 19(5): 665-7) and is not expected to contribute to the peripheral neuropathy associated with HIV infection.

Vitamin K (Raya, A. et al, (1995) Free Radic. Biol. Med. 19(5): 665-7) is another multivitamin subject to oxidation and is therefore prone to the production of free radicals associated with increased HIV activity. This oxidation can be prevented by Vitamin C (Myhrstad, M. C. et al, (2002) Free Radic. Bio. Med. 32(5): 396-93; Boots, A. W. et al, (2003) Biochem. Biophys. Res. Commun. 308(3): 560-5; Kubow, S. and Wells, P. G. (1989) Mol. Pharmacol. 35(4): 504-11), which also protects quercetin from oxidation. Quercetin has multiple functions including, but not necessarily limited to, protection against the endothelial cell dysfunction (Centurelli, M. A. and Abate, M. A., (1997) Ann. Pharmacother. 31(5): 639-42; Nooroozi, M. et al, (1988) Am. J. Clin. Nutr. 67(6): 1210-8) induced by insulin resistance that has been reported in HIV infection without antiretroviral therapy (Shevitz, A. et al, (2001) AIDS 15(15: 1917-30), but only if protected from oxidation.

Quercetin not only increases GSH production, but also reduces lipid peroxidation, which is a major source of oxidative stress and increased HIV activity (Su, J. F. et al, (2003) Biomed. Environ. Sci. 16(1): 1-8), both systemically and in the GI tract, a major reservoir of HIV infection (Washington, C. B. et al, (1998) J. Acquir. Immune Defic. Syndr. Hum. Retrovirol. 19(3): 203-9; Kotler, D. P. (1989) Adv. Intern. Med. 34: 43-71). GSH and quercetin can re-establish normal gastrointestinal antioxidant status within 7 days (Galvez, J. et al, (1994) Gen. Pharmacol. 25(6): 1237-43). Further, GSH and quercetin improve liver antioxidant status by increasing glutathione production that is important in subjects co-infected with hepatitis C and/or B (Molina, M. F. et al, (2003) Biol. Pharm. Bull. 26(10): 1398-1402) when protected from oxidation by Vitamin C. In addition, quercetin, when protected from oxidation, decreases DNA strand breaks in activated lymphocytes that has been reported to result in decreased $CD4^+$ and $CD8^+$ T-cell function, increased lymphocyte death and increased HIV activity (Noroozi, M. et al, (1998) Am. J. Clin. Nutr. 67(6): 1210-8; Szeto, Y. T. and Benzie, I. F., (2002) Free Radic. Res. 36(1): 113-8). Vitamins C, B6 and GSH protect cutaneous sensory neurons, which can be damaged by phenytoin and, as noted above for GSH, may mitigate the peripheral neuropathy associated with HIV infection (Wells, P. G. et al, (1997) Mutat. Res. 396(1-2): 65-78).

Quercetin has also been reported to decrease the absorption of Vitamin C (Fiorani, M. et al, (2001) Free Radic. Res. 34(6): 1749-51; Vrijsen, R. et al, (1988) J. Gen. Virol. 69(Pt. 7) 1749-51), which in turn is required to prevent quercetin oxidation, as well as reducing the absorption of Vitamin E (Jan, C. Y. et al, (1991) Biochim. Biophys. Acta 1086(1): 7-14). This is obviated by the compositions of the present invention and is particularly important as Vitamin C and Vitamin E both regenerate reduced GSH after oxidation, a process which would otherwise be inhibited by reducing the activity of glutathione reductase (Mak, S. et al, (2002) Am. J. Physiol. Heart Circ. Physiol. 282: H2414-H2421; Noroozi, M. et al, (1998) Am. J. Clin. Nutr. 67(6): 1210-8) and, if not protected by Vitamins C and E, would foster GSH oxidation and loss of its antioxidant functions.

Quercetin (Hu, H. L. et al, (2000) Mech. Aging Dev. 121 (1-3): 217-30) has also been shown to decrease aberrant B cell function in HIV as well as decrease endothelial dysfunction when protected from oxidation by Vitamin C & E, which is important as endothelial dysfunction is associated with insulin resistance (Fiorani, M. et al, (2001) 34(6): 639-48) and 35% of subjects with HIV, even without ART, have impaired glucose tolerance (Shevitz, A. et al, (2001) AIDS 15(15): 1917-30; Kotler, D. P. (2003) AIDS Read. 13(4 Suppl): S5-S9). In addition, it has been reported to decrease diabetic nephropathy (Anjaneyulu, M. and Chopra, K. (2004) Clin. Exp. Pharmacol. Physiol. 31(4): 244-248; Coldiron, A. D. Jr., et al, (2002) J. Biochem. Mol. Toxicol. 16(4): 197-202) and is believed to protect against HIV nephropathy. Furthermore, quercetin is well absorbed in the jejunum (66%) (44), while the remainder is excreted.

The return to normal oxidative status in the gastrointestinal tract (a major reservoir of HIV) after 7 days (Myhrstad, M. C. et al, (2002) Free Radic. Biol. Med. 32(5): 386-93; Galvez, J. et al, (1994) Gen Pharmacol. 25(6): 1237-43) in animals treated with quercetin can be explained, in part, by the increase in GSH levels induced by quercetin. Quercetin can also decrease glucose absorption (Song, J. et al, (2002) J. Biol. Chem. 277(18): 15252-60) if protected from oxidation by Vitamin C, and can synergize with the effect of phenytoin (Cudworth, A. G. and Barber, H. E., (1975) Eur. J. Pharmacol. 31(1): 23-8), which decreases insulin release from the pancreas (Fuenmayor, N. T., et al, (1997) J. Cardiovasc. Pharmacol. 30(4): 523-7). Furthermore, the presence of a calcium channel blocker, such as verapamil, enhances insulin sensitivity. Together these components function to protect, at least partially, against the insulin resistance, impaired glucose tolerance (Wahl, M. A. et al, (1998) Exp. Clin. Endocrinol. Diabetes 106(3): 173-7) and resultant endothelial dysfunction and increased cardiovascular events (Mak, I. T. et al, (1995) Biochem. Pharmacol. 50(9): 1531-4) in HIV reported even in the absence of ART (Shevitz, A. et al, (2001) AIDS 15(15): 1917-30; Kotler, D. P. (2003) AIDS Read. 13(4Suppl): S5-S9).

In addition, a number of components comprising the compositions of the present invention reinforce or are additive/synergistic to the mechanisms mentioned herein. These include, but are not necessarily limited to, replacement of $Mg^{2+}$ and $Zn^{2+}$, which are decreased by phenytoin (Wells, P. G. et al, (1997) Mutat. Res. 396(1-2): 65-78). $Mg^{2+}$ decreases nuclear factor κB (NF-κB), IL-1, IL-6 and tumor necrosis factor-α (TNF-α) production and excretion, which together with Verapamil (Yokoyama, T. et al, (2003) Life Sci. 72(110: 1247-57) and DHEA, decrease HIV activity as well as protect against endothelial dysfunction (Shogi, T. et al, (2003) Magnes. Res. 16(2): 111-9). Endothelial dysfunction can be associated with insulin resistance and increased cardiovascular events by decreasing oxidative stress (Rubio-Luengo, M. A. et al, (1995) Am. J. Hypertens. 8(7): 689-695).

The addition of $Ca^{2+}$, $Mg^{2+}$, boron and Vitamin D in the compositions of the present invention can also protect against bone loss associated with long-term use of phenytoin and which occurs in HIV even in the absence of ART (Shevitz, A. et al, (2001) AIDS 15(15): 1917-30). In addition, chromium piconolate in the inventive compositions of the invention can enhance insulin activity by interaction with insulin receptors of the cell surface (Kims, D. S. et al, (2002) Metabolism 51(5): 589-94) and increases GLUT-4 glucose transporter translocation required to maximize insulin activity (Cefalu, W. T. et al, (2002) J. Nutr. 132(6): 1107-14). Furthermore, reducing insulin resistance by the additive or synergistic mechanisms described herein can reduce endothelial dysfunction, decrease triglyceride levels, and decrease platelet aggregation (Diabetes Educ. (2004) Suppl: 2-14).

Addition of chromium can inhibit reactive oxidative stress by improving insulin's function and improving or bolstering immune function (Shrivastava, R. et al, (2002) FEMS Immunol. Med. Microbiol. 34(1): 1-7) while $Zn^{2+}$ in the compositions of the invention has additive effects in decreasing insulin resistance, low density lipoprotein levels, which decreases atherogenesis and increased cardiovascular and cerebral vascular aberrations which have been reported in HIV/AIDS even in the absence of ART (Shevitz, A. et al, (2001) AIDS 15(15): 1917-30; Kotler, D. P. (2003) AIDS Read. 13(4 Suppl): S5-S9).

Verapamil has a number of other functions including anti-HIV activity, as well as reducing some of the metabolic dysfunctions that are an obligate part of HIV infection. It also prevents biliary excretion of Vitamin E (Mustacich, D. J. et al, (1998) Arch. Biochem. Biophys. 350(2): 183-92), which is required to replenish reduced glutathione, and restores the sensitivity of the malaria parasite *Plasmodium falciparum* to chloroquine therapy by blocking the multidrug resistance pump P-glycoprotein (Vezmar, M. and George, E. (1998) Biochem. Pharmacol. 56(6): 733-42; Siddiqi, N. J. and Alhomida, A. S. (1999) In Vivo 13(6): 547-50). This restoration of sensitivity can be enhanced by both DHEA and glutathione (Freilich, D. et al, (2000) Am. J. Trop. Med. Hyg. 63(5-6): 280-3). This restoration is particularly advantageous, as it decreases the increased oxidative stress in the African population infected with various forms of malaria and additionally co-infected with HIV, which, if left untreated, can result in anemia and an obligate increase in oxidative stress as well as progression of HIV. The decreased oxidative stress in subjects coinfected with HIV and malaria can also be further decreased by inclusion or administration of Vitamins A, C and E, which are reduced in both malaria (Farombi, E. O. et al, (2003) Drug Chem. Toxicol. 26(1): 21-6) and HIV (Fawzi, W. W. et al, (2004) N. Engl. J. Med. 351: 23-32).

Chloroquine, especially at high doses (>2250 mg day; PDR Volume # 59, page 2984) or used over a prolonged period can result in hepatic, renal, and retinal toxicity. α-lipoic acid is another multivitamin component that can be included in the compositions and methods of the present invention. α-lipoic acid protects against the hepatic (Pari, L. and Murugavel, P. (2004) J. Appl. Toxicol. 24(1): 21-6; Murugavel, P. and Pari, L. (2004) Ren. Fail. 26(5): 517-24) and renal (Toler, S. M. (2004) Exp. Biol. Med. (Maywood) 229(7): 607-15) toxicity associated with long-term or high-dose chloroquine use, while Vitamin C, E, GSH and other antioxidants in the compositions of the herein described invention protect against chloroquine induced retinopathy caused by increased oxidative stress (Dale, M. M. and Ladd, R. (1984) Br. J. Pharmacol. 83(1): 293-8).

This is particularly significant, as chloroquine increases the lysosomal pH, thereby decreasing lymphocyte activation and HIV activity (Choo, E. F. et al, (2000) Drug Metab. Dispos. 28(6): 655-660). This function and the reported decrease in the budding of certain herpesviruses by chloroquine, which has been reported to increase HIV replication of latest in part by increasing IL-6 production and excretion (Washington, C. B. et al, (1998) J. Acquir. Immune Defic. Syndr. Hum. Retrovirol. 19(3): 203-9; Mocroft, A. et al, (1999) AIDS 13(8): 943-50) act together to reduce IL-6 production and excretion and the obligate decrease in HIV replication. These mechanisms are reinforced by the function in DHEA, which also decreases IL-1, IL-6 and TNF production (Meierjohann, S. et al, (2002) Biochem. J. 368(Pt. 3): 761-8; Mak, I. T. et al, (1994) Am. J. Physiol. 267(5 Pt. 1): C1366-70; Magwere, T. et al, (1997) Free Radic. Biol. Med. 22(1-2): 321-7; Abdel-Gayoum, A. A. et al, (1992) Pharmacol. Toxicol. 71(3 Pt. 1): 161-4).

In addition to its role in reducing HIV replication, chloroquine has a number of other functions. In African populations with a high prevalence of malaria and the obligate anemia arising from malaria infection is an independent predictor of HIV progression (Belperio, P. S. and Rhew, D. C. (2004) Am. J. Med. 116 Suppl. 7A: 27S-43S) and ultimately decreases quality of life. Chloroquine treatment with or without the conversion of resistant malaria by verapamil (Vezmar, M. and George, E. (1988) Biochem. Pharmacol. 56(6): 733-42; Siddiqi, N. J. and Alhomida, A. S. (1999) In Vivo 13(6): 547-50), when administered with DHEA and GSH (Safeukui, I. et al, (2004) Biochem. Pharmacol. 68(10): 1903-10), can reverse the anemia and restore GSH levels. Similarly, chloroquine activity can be enhanced by GSH (Galvez, J. et al, (1994) Gen. Pharmacol. 25(6): 1237-43) by decreasing the oxidative stress noted in $Mg^{2+}$ deficiency and malarial infection which is common in HIV (Herzenberg, L. A. et al, (1997) Proc. Natl. Acad. Sci. USA 94: 1967-1972; Tuchweber, B. et al, (1976) Arch. Pathol. Lab. Med. 100(2): 100-5) and replaced by IV.

Furthermore, long-term use of Chloroquine has been reported in animal studies to reduce GSH and selenium levels (Herzenberg, L. A. et al, (1997) Proc. Natl. Acad. Sci. USA 94: 1967-1972). This is important as reduced GSH and selenium levels (Herzenberg, L. A. et al, (1997) Proc. Natl. Acad. Sci. USA 94: 1967-1972) increase HIV activity and progression. This potential effect can be obviated by the components comprising the compositions of the present invention.

Compositions of matter, in accordance with preferred embodiments of the invention can comprise in admixture: quercetin or one of its derivatives, an anti-convulsant component, at least one calcium channel blocker component; a quinoline component; a multivitamin component; derivatives of these components, such as pharmaceutically acceptable salts, hydrochlorides, tartrates, malates, maleates, chelates and metabolites thereof and a pharmaceutically acceptable systemic carrier for oral administration. The invention also comprises a combination of the metabolites of these three components. The components can be provided in solid or liquid form, as particle suspensions or in water or alcohol based solutions. The compositions can be formulated for oral, topical, intrathecal, intramuscular, subcutaneous, epicutaneous, intranasal, aerosol, or parenteral administration, although oral administration is preferred. The components of the composition should be provided in therapeutically effective amounts to treat viruses, such as HIV. In a weight ratio of about 100-240 mg $Ca^{2+}$ channel blocker (or metabolite): about 200-250 mg chloroquine, quinoline, quinoline/quinone: about 100-300 mg anticonvulsant: and about 1200-2400 mg quercetin.

The invention also comprises administration of a composition in accordance with preferred embodiments of the invention to a mammal suffering from a viral infection such as HIV, in sufficient dosage to reduce and treat such infection.

It has been demonstrated that inhibition of calcium ($Ca^{2+}$) influx during cell activation by blocking voltage regulated $Ca^{2+}$ channels results in decreased symptoms in subjects suffering from hyperactive immune systems. This decreased activation involves decreased interleukin synthesis and decreased mitogen reactivity. In vitro studies of the effect of $Ca^{2+}$ channel blockers on HIV infection both in HIV adapted cell lines (HUT/H9) as well as acutely infected peripheral blood lymphocytes revealed a 50-60% reduction in HIV production (HIV PCR RNA) and ICD p24$^{gag}$ antigen at pharmacologically achievable concentrations. A second, non-competitive complementary class of drugs was sought which would provide an additive or resulting synergistic effect.

In experiments similar to those described above, the addition of effective amounts of chloroquine to either H4T infected cells or acutely infected peripheral blood mononuclear cells (PBMC), reduced viral activity (replication) by 20-40%. In similar cultures with pharmacologically achievable concentrations of verapamil, a calcium blocker and chloroquine, viral activity was reduced by 75-85%. In concert with a $Ca^{2+}$ channel blocker therefore, the net effect is to reduce the activation of NF-κB from the cell as well as the HIV TAT engine and suspend the uncoated virus in the hostile milieu of the cytosol. It has been shown in multiple studies that untranslated, unintegrated virus is most susceptible to degradation and the longer the virus remains in this vulnerable state, the less replication competent it becomes.

In experiments similar to those described above, a standardized extract of quercetin (containing 1-10 μg/ml quercetin available from Sigma Aldrich) revealed a 5-20% reduction of HIV activity. When added to preferred concentrations (30 μg/ml of Verapamil and 10 μg/ml chloroquine) the composition achieved 85-95% reduction of HIV activity. It is believed that quercetin decreases viral activity by weakly inhibiting CD4 binding as well as the conversion of RNA to DNA preventing integration of the viral DNA in the genome. This occurred in a non cytotoxic manner with concentrations in vitro, which are easily achievable in vivo and resulting in at least a two log decrease in viral activity. This is a much larger decrease in comparison to current HIV drugs such as AZT, D4T, DDI, where the viral activity decreases 0.4-0.7 log.

This discovery of meaningful interaction between $Ca^{2+}$ channel blockers and chloroquine and its analogues as well as the benign side effect profile of quercetin represents a safe and potentially effective inexpensive alternative to current HIV therapy for the over 40,000,000 subjects afflicted worldwide who cannot afford the current HAART therapy.

Initial studies on adults indicate that the following range for unit dosages for each of the ingredients would be appropriate.

| | |
|---|---|
| Phenytoin | 100-300 mg |
| Verapamil | 5-500 mg, preferably 100-240 mg |
| Chloroquine | 200-250 mg |
| Quercetin | 1200-2400 mg |
| Multivitamin | four capsules of Immune Vitality or equivalent composition |

These dosages should be administered 1-4 times a day, preferably one time per day. It is also envisaged that lower dosages may be appropriate for children. The adjustment of the dosages according to body weight and metabolism would be apparent to those skilled in the art. Compositions including the active ingredients recited above can be effective in reducing viral activity in mammals. It is preferred that each component be present at a weight ratio of 100 to 240 mg $Ca^{2+}$ channel blocker to about 200 to 250 mg quinoline, quinoline/quinone or intermediate to about 1200-2400 mg quercetin. As used herein, the identification of a drug or other therapeutic compound is intended to refer also to pharmaceutically effective forms of the drug, such as salt forms, hydrochlorides, tartrates, maleates, malates, succinates, chelates and so forth to establish sustained release of one or more of the active ingredients, which are used in the administration of the drug.

Any suitable antagonist, generally, of neuronal voltage-dependent $Ca^{2+}$ channels can be effective under certain conditions. Preferred calcium channel antagonists include, but are not limited to, the following drugs, of which the most preferred are those that are capable of crossing the blood brain barrier, for example, nimodipine (Miles Pharmaceuticals, West Haven, Conn.), Smith Kline drug no. 9512 (Smith Kline, French-Beecham, Philadelphia, Pa.), and diproteverine (Smith Kline, French-Beecham). Less preferred antagonists are those that are less CNS permeable, for example, verapamil (Calan, G. D. Searle & Co., Chicago, Ill.; Isoptin, Knoll, Whippany, N.J.), nitrendipine, and diltiazem (Cardizem, Marion, Kansas City, Mo.). Other $Ca^{2+}$ channel antagonists which may be useful are mioflazine, flunarizine, bepridil, lidoflazine, CERM-196, R 58735, R-56865, Ranolazine, Nisoldipine, Nicardipine, PN200-110, Felodipine, Amlodipine, R-(−)-202-791, and R-(+) Bay K-8644 (Miles, Bayer), whose chemical formulae are described in Boddeke et al., Trends Pharm. Sci. (1989) 10:397 and Triggle et al., Trends Pharm. Sci. (1989) 10:370, incorporated by reference.

Verapamil is a known $Ca^{2+}$ channel blocker and is a competitive inhibitor of P-glycoprotein, as described by Inoue et al, (1993) J. Biol. Chem. 268(8): 5894-8; Hunter, J. et al. (1993) Pharm. Res. 10(5): 743-9; Hori, R. et al, (1993) J. Pharmacol. Exp. Ther. 266(3): 1620-5; Pourtier-Manzanedo et al, (1992) Oncol. Res. 4(11-12): 473-80; Boesch, D. & Loor, F. (1994) Anticancer Drugs 4(2): 223-9; Zacherl et al, (1994) Cancer Chemother. Pharmacol. 34(2): 125-32.; Shirai et al. (1991); Morris et al. (1991); Muller et al, (1994) Int J Cancer. 56(5): 749-54; and Miyamoto et al, (1992) Anticancer Res. 12(3): 649-53. Thalhammer et al ((1994) Eur. J. Pharmacol. 270(2-3): 213-20) showed that P-glycoprotein-mediated transport of the cationic dye acridine orange, across the bile canaliculi was inhibited by cyclosporine A and verapamil. The ATP-15 dependent transport of amphiphilic cations across the hepatocyte canalicular membrane by p-glycoprotein was also studied by Muller et al. (1994). Transport of permanently charged amphiphilic cations was inhibited by verapamil, quinidine and the antibiotic, daunorubicin. Bear (1994) showed that verapamil, colchicine, vinblastine and daunomycin (50 μM) blocked an outwardly-rectifying chloride channel that was proposed to be associated with p-glycoprotein expression. Ohi et al. ((1992) Cancer Chemother Pharmacol. 30 Suppl: S50-4) used the calcium-channel blocker, verapamil, with adriamycin in chemotherapy for superficial bladder cancer. Five ampules (10 ml) of injectable verapamil were given. Verapamil hydrochloride is benzene-acetonitrile-α-[3-[[2-(3,4-dimethoxyphenyl)ethyl]-methylamino]propyl]-3,4-dimethoxy-α-(1-methylethyl) hydrochloride; also termed CALAN™ and ISOPTIN™, and available from Searle, Knoll and Parke-Davis.

Verapamil is more than 90% absorbed, but only 20 to 35% of the dose reaches the system because of extensive hepatic first-pass metabolism. It is bound approximately 90% to plasma proteins. The liver metabolizes it rapidly to nor-verapamil and traces of several other metabolites. About 70% of a dose is excreted in urine as metabolites, and 16% of a dose appears in the feces within 5 days; less than 5% is excreted unchanged. The effects of verapamil are evident within 30 to 60 minutes of an oral dose. Peak effects of verapamil occur within 15 minutes of its intravenous administration. The half-life is 1.5 to 5 hours in normal persons but may exceed 9 hours during chronic therapy. In subjects with cirrhosis of the liver, the half-life may be increased to 14 to 16 hr. The half-life is increased in subjects with liver disease, due, in part, to an increased volume of distribution. Saturation kinetics has been observed after repeated doses.

Preferred doses include: intravenous, adults, initially 5 to 10 mg (0.075 to 0.15 mg/kg) over a period of 2 min (3 min in the elderly), followed by 10 mg (0.150 mg/kg) after 30 min, if necessary; children, up to 1 year, initially 0.1 to 0.2 mg/kg over 2 min (with ECG monitoring), repeated after 30 min. if necessary; 1 to 15 years, initially 0.1 to 0.3 mg/kg, not to exceed 5 mg, repeated after 30 min, if necessary. Oral, adults, 80 mg 3 or 4 times a day or 240 mg once a day in sustained-released form, gradually increased to as much as 480 mg a day, if necessary. Verapamil is available in injectable dosage forms of 5 mg/2 mL and 10 mg/4 mL; tablet dosage forms of 40 mg, 80 mg and 120 mg; and sustained-release tablets of 240 mg. Preferred amounts of verapamil in the compositions and methods of the present invention are in the range of 100-240 mg.

This invention also relates also to pharmaceutical dosage unit forms for systemic administration (oral, topical administration, transdermal including controlled release of medication for long-term treatment or prophylaxis), which are useful in treating mammals, including humans. The term "dosage unit form" as used herein and in the claims refers to physically discrete units suitable as unitary dosage for mammalian subjects, each unit containing a predetermined quantity of the essential active ingredients discussed herein, calculated to produce the desired effect in combination with the required pharmaceutical means which adapt said ingredient for systemic administration.

Examples of dosage unit forms in accordance with this invention are tablets, capsules, powders, dragees, and orally administered liquid preparations in liquid vehicles, elixirs, sprays, aerosols, suppositories, and dry or lyophilized preparations for the extemporaneous reconstitution of the dry preparations in a liquid vehicle or for nasal administration by inhalation. Preferably, the compositions can be combined and simultaneously or concurrently administered with a surfactant, a carrier, solvent, excipient, or diluent. Such additives are known to those of skill in the art and can be found in the Handbook of Pharmaceutical Excipients (4$^{th}$ Edition, Rowe, R. C. (eds) Pharmaceutical Press, Chicago, Ill.). As an example, such carriers can include hydroxypropylmethylcellulose (HPMC), hydroxypropylcellulose, silicon dioxide, and plasticizers such as polyethylene glycol, polyethylene oxide, among others.

Solid diluents or carriers for the solid oral pharmaceutical dosage unit forms are selected from the group consisting of lipids, carbohydrates, proteins and mineral solids, for example, starch, sucrose, lactose, mannitol, kaolin, dicalcium phosphate, polyvinylpyrrolidone, crospovidone, gelatin, acacia, xanthan gum, corn syrup, corn starch, micronized starch, colloidal silica, talc and the like. Capsules, both hard and soft, are formulated with conventional diluents and excipients, for example, edible oils, talc, calcium carbonate, calcium stearate, magnesium stearate and the like. Liquid pharmaceutical preparations for oral administration may be prepared in water or aqueous solutions such as phosphate buffered saline (PBS) which advantageously contain suspending agents, such as for example, sodium carboxymethylcellulose, methylcellulose, acacia, polyvinyl pyrrolidone, crospovidone, polyvinyl alcohol and the like.

Such preparations should be stable under the conditions of manufacture and storage, and ordinarily contain in addition to the basic solvent or suspending liquid, preservatives in the nature of bactericidal and fungicidal agents, for example, parabens, chlorobutanol, benzyl alcohol, phenol, thimerosal, and the like. In many cases it is preferable to include isotonic agents, for example, sugars such as lactose or mannitol, or sodium chloride. Carriers and vehicles include vegetable oils, dimethyl sulfoxide (DMSO), water, ethanol, and polyols, for example, glycerol, propylene glycol, liquid polyethylene glycol, polyethylene oxide, and the like.

The pharmaceutical dosage unit forms are prepared in accordance with the preceding general description to provide an effective amount of the essential active ingredients per dosage unit form in admixture with the means for adaptation to systemic administration. In general, the unit dose form will contain 3 to 73 percent by weight of the essential active ingredients.

It will be appreciated that the exact dosage of the essential active ingredient constituting an effective amount for treatment of a mammal according to the method of the invention will vary greatly depending on the specific nature of the clinical condition being treated, severity of the condition, species of mammal, age, weight and condition of the mammal, mode of administration of the dosage form and the specific formulation being administered. The exact dose required for a given situation may be determined by administration of a trial dose and observation of the clinical response. In general, an effective amount to be administered will be within a range of from about 0.1 mg per kg to mg per mg per kg of body weight of the recipient, daily. Preferably 0.5 mg/kg to about 25 mg/kg daily is provided. In most instances, a single month of administration will affect a noticeable response and bring about the result desired. In cases such as the treatment of immunological conditions however, it may be desirable to repeat the administrations several times daily over longer periods of time.

The invention will now be further described by way of the following non-limiting Examples, given by way of illustration of various embodiments of the invention and are not meant to limit the present invention in any fashion.

EXAMPLES

Example 1

A mixture of the following ingredients was prepared by hand mixing:

| Ingredient | Quantity |
| --- | --- |
| Verapamil | 100-240 mg |
| Chloroquine | 200-250 mg |
| Quercetin | 1200-2400 mg |
| Phenytoin | 100-300 mg |

One dosage given orally, 1-4, preferably 1-2 times a day is useful in the relief of immunodeficiency in adult humans provoked by infective disease, or other etiological causes. When administered to a human adult suffering from HIV, 1 to 4 dosage units daily, the level is adjusted upward to a normal range.

It has been shown that the administration of the above dosage unit mixed 1-4 times (preferably 1 or 2 times) a day is useful in the relief of immunodeficiency in adult humans provoked by infective disease, or other etiological causes.

Example 2

The following were prepared:

| Composition | Amount | Component |
| --- | --- | --- |
| MP-1: A | 35 µg/ml | Verapamil (35 µg) |
| MP-1: B | 10 µg/ml | Chloroquine (10 µg) |
| MP-1: C | 4 µg/ml | Quercetin (4 µg) |

The effects of administration of the above after 4 days of administration on the viral load of peripheral blood lymphocytes infected with a laboratory adapted HIV virus are shown in FIG. 1. As can be seen, MP-1:MIX: and MP-1:[fraction (½)]MIX exhibited a synergistic therapeutic effect and surpassed the effectiveness of AZT.

Example 3

Figure 2:
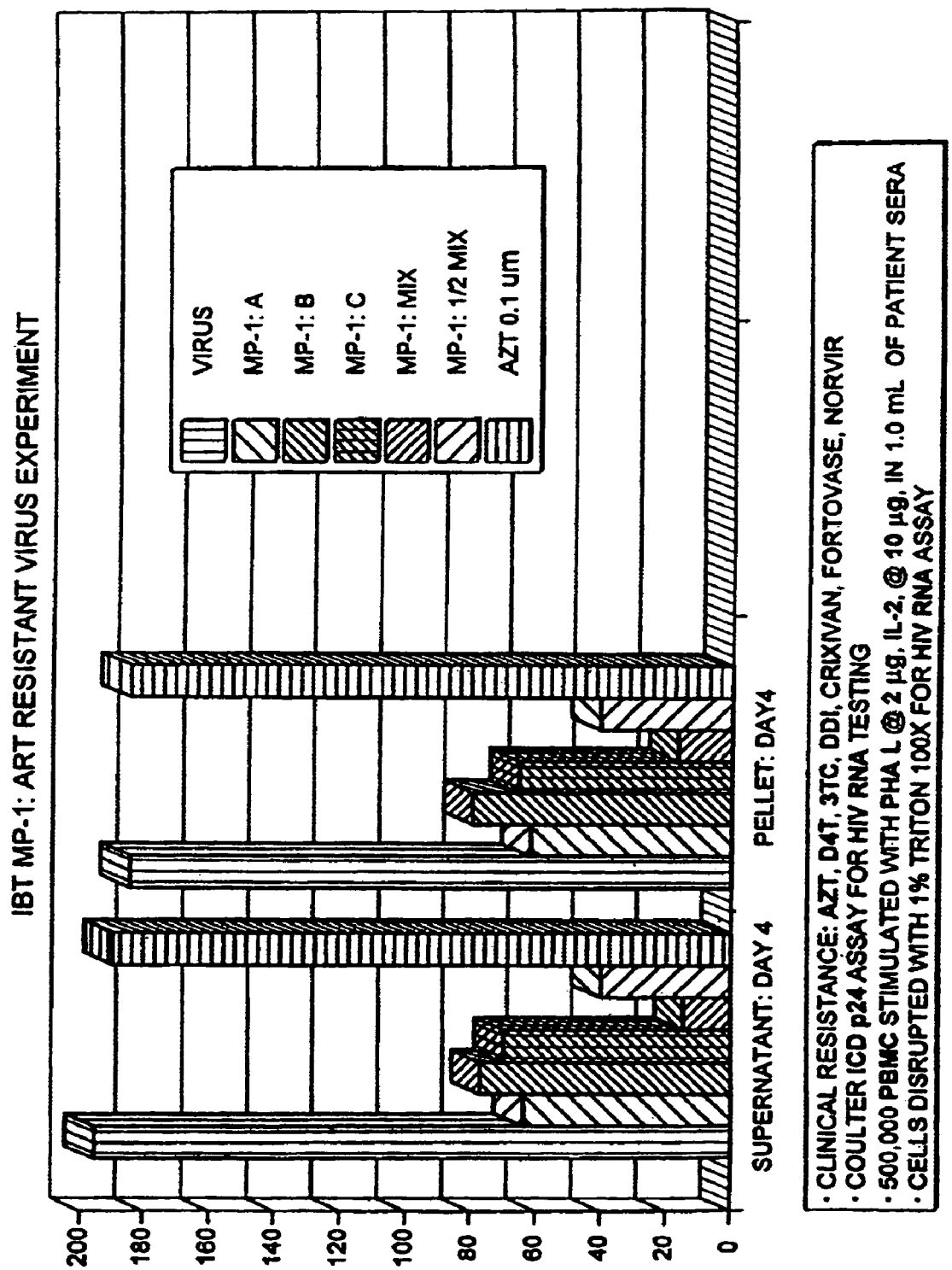
FIG. 2 is a graph depicting the results of 20 experiments on the effects of compositions in accordance with embodiments of the invention, on the viral load (measured by $p24^{gag}$ ICD) of peripheral blood lymphocytes infected with a highly active anti-retroviral therapy (HAART) resistant clinical viral isolate.

The effects of administration of the above after 4 days of administration on the viral load of peripheral blood lymphocytes infected with a HAART resistant clinical viral isolate are shown in FIG. 2. A synergistic therapeutic effect and superiority to AZT was again demonstrated.

Example 4

Figure 3:
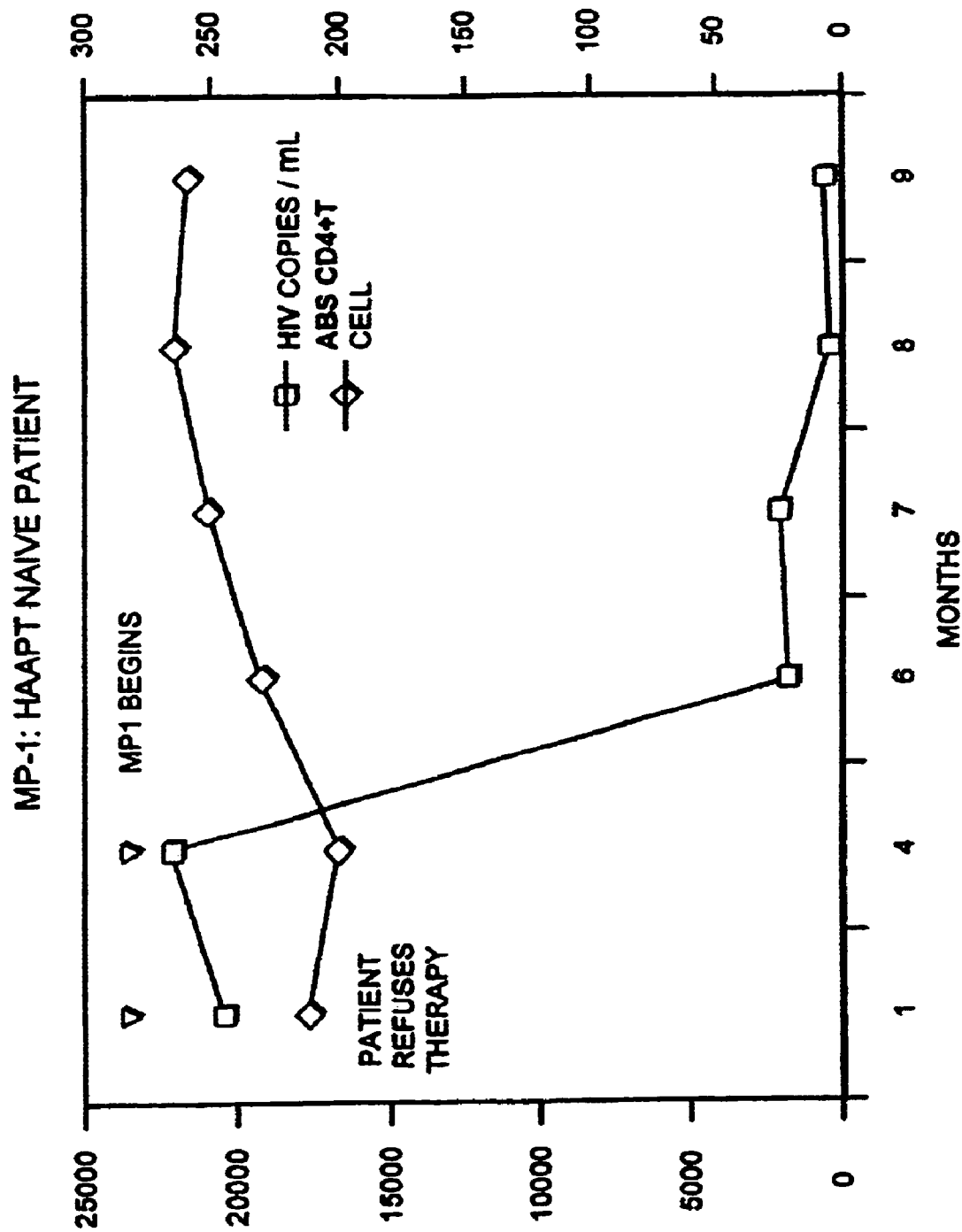
FIG. 3 is a graph showing the effects of verapamil and quercetin on the CD4 count and viral load of a hypertensive subject who refused anti-retroviral therapy.

The effects of verapamil SR 180 and quercetin (150 mg) on the CD4 count and viral load of a hypertensive subject who refused anti-retroviral therapy are shown in FIG. 3. Again, the benefits of the invention were demonstrated.

It is understood that the proportions and ingredients may be adjusted for the stage of illness as well as the subject's tolerances of the individual components. Further, it is understood that the metabolites of a calcium channel blocker or quinoline may be used in appropriate forms. Further it is also understood that the active components of quercetin such as polyphenols, glycosides, flavonoids, and bio-flavonoids may be extracted and used in appropriate proportions to yield desired results.

Example 5

As described above, both HIV and the H5N1 strain of avian influenza are enveloped single-stranded RNA viruses. There are several other parallels between HIV and H5N1. For example, upon cellular entry both HIV and the H5N1 virus promote a brisk influx of calcium. In addition, glutathione levels are believed to be predictive of death in both HIV and H5N1 infection, and GSH has protective effects against H5N1 in vitro. Furthermore, both HIV and H5N1 infection cause a major brisk immune response. HIV infects monocytes and CD4 cells and kills the latter by both direct cytotoxicity and apoptosis which attenuates the immune response. H5N1 infects epithelial cells and causes an unbridled pro-inflammatory immune response inducing a so-called "cytokine storm". The induction of this cytokine storm is one the major causes of pathogenicity as it leads to death of epithelial cells, acute respiratory distress syndrome and, in many cases death.

In light of the above similarities, it was hypothesized that the novel compositions of the present invention might be effective against both HIV and H5N1 infections, and that furthermore, the compositions of the present invention might be effective in the treatment or amelioration of other diseases caused be single-stranded RNA viruses, and/or other diseases and medical conditions characterized by the induction of a "cytokine storm".

Experiments were performed in which peripheral blood mononuclear cells ("PBMCs") were treated in vitro either with glass beads or with the plant lectin phytohemagglutinin ("PHA") which is similar to Influenza hemagglutinin A, and also treated with a compositions of the present invention. In the present example, cells were treated with a composition of the present invention referred to as "PBS119" comprising verapamil 120 mgs, dilantin 200 mgs, chloroquine 100 mgs, and quercetin 1200 mgs.

Treatment of cells with glass beads beads and/or cross-linked dextrans such as Sephadex G-25 results in an inflammatory response including macrophage activation and the release of pro-inflammatory cytokines from cells. (See Blanckmeister & Sussdorf, "Macrophage activation by cross-linked dextran," Journal of Leukocyte Biology, Volume 37(2), pages 209-219). Treatment of cells with PHA is known to stimulate cytokine release. (See Greaves & Janossy, Transplant. Rev. Volume 11, page 87 1972). Thus, treatment of cells with either glass beads and/or PHA provides a useful surrogate for the type of immune activation and cytokine storm induced by H5N1 infection. Furthermore, because the "cytokine storm" is believed to be one of the major causes of death from H5N1 infection, the ability of a drug to reduce the cytokine storm suggests that that drug will be useful in treating H5N1 infection, and also infection with other agents that cause a cytokine storm.

Approximately 1 million PBMCs in Complete media (consisting of Roswell Park Memorial Institute (RPMI) 1640 media containing 10% fetal calf serum (FCS), penicillin/streptomycin) were used for each experimental group. Cells were exposed to either 2 μg of PHA-L or 10 million glass beads. Cells in the experimental groups were then treated with PBS119. Cells in both the control (untreated) and experimental groups were incubated for 96 hours at 37° C. in a 5% $CO_2$ atmosphere. The cells were then harvested, washed three times with physiological phosphate buffered saline, pelleted by centrifugation, and exposed to 100 μgs of anti-CD4 and anti-CD69 antibodies (Becton Dickinson, Mountainview, Calif.). Anti-CD4 antibodies were labeled with a green fluorescent marker and anti-CD69 antibodies were labeled with a red fluorescent marker. Flow cytometry was then performed using a FACS-Caliber flow cytometer (Becton Dickinson, Mountainview, Calif.) to detect green and red fluorescence. The amount of activated cells was quantified by dividing the number of CD4/CD69 positive cells by the total number of CD4 positive cells. Cells treated with the compositions of the present invention exhibited a 67 to 75% decrease in immune activation as compared to untreated controls.

The data suggests that the compositions of the present invention can be used to decrease immune reactivity associated with H5N1 infection, and to reduce or ablate the "cytokine storm" and the resultant development of acute respiratory distress and possibly death in H5N1 infected individuals. The data also suggests that the compositions of the present invention could be useful for treating other infections and diseases characterized by immune reactivity and the induction of a cytokine storm.

It should be noted that compositions according to the present invention may vary from the exact amounts and ratios used in this example. For example, compositions can be used in which the amount of verapamil is in the range 80-240 mgs, the amount of dilantin is in the range 100-300 mgs, the amount of chloroquine is in the range 100-250 mg, and the amount of quercetin is in the range 1200-2400 mgs. Other amounts of these components may also be used. In addition, other suitable calcium channel blockers can be used in the place of verapamil, other suitable anticonvulsants can be used in the place of dilantin, other suitable quinolines can be used in the place of chloroquine, and quercetin derivatives may be used in the place of quercetin. It is understood that the exact proportions and ingredients may be adjusted depending on various factors including the stage of illness as well as the subject's tolerances of the individual components.

It should also be noted that when treating patients, a multivitamin component should also be used as this will decrease the metabolic consequences of the PBS119 components. The multivitamin component has several beneficial effects for example increasing levels of Glutathione, DHEA, selenium, zinc, vitamins C, A and beta carotene.

Example 6

Therapeutically effective amounts of the compositions of the present invention, including those described in each of the above examples and throughout the specification of the present application, are administered to patients infected with avian influenza, including the H5N1 strain of avian influenza in order to treat the infection. It is understood that the proportions and ingredients may be adjusted depending on various factors including the stage of illness as well as the subject's tolerances of the individual components.

Example 7

Figure 4:
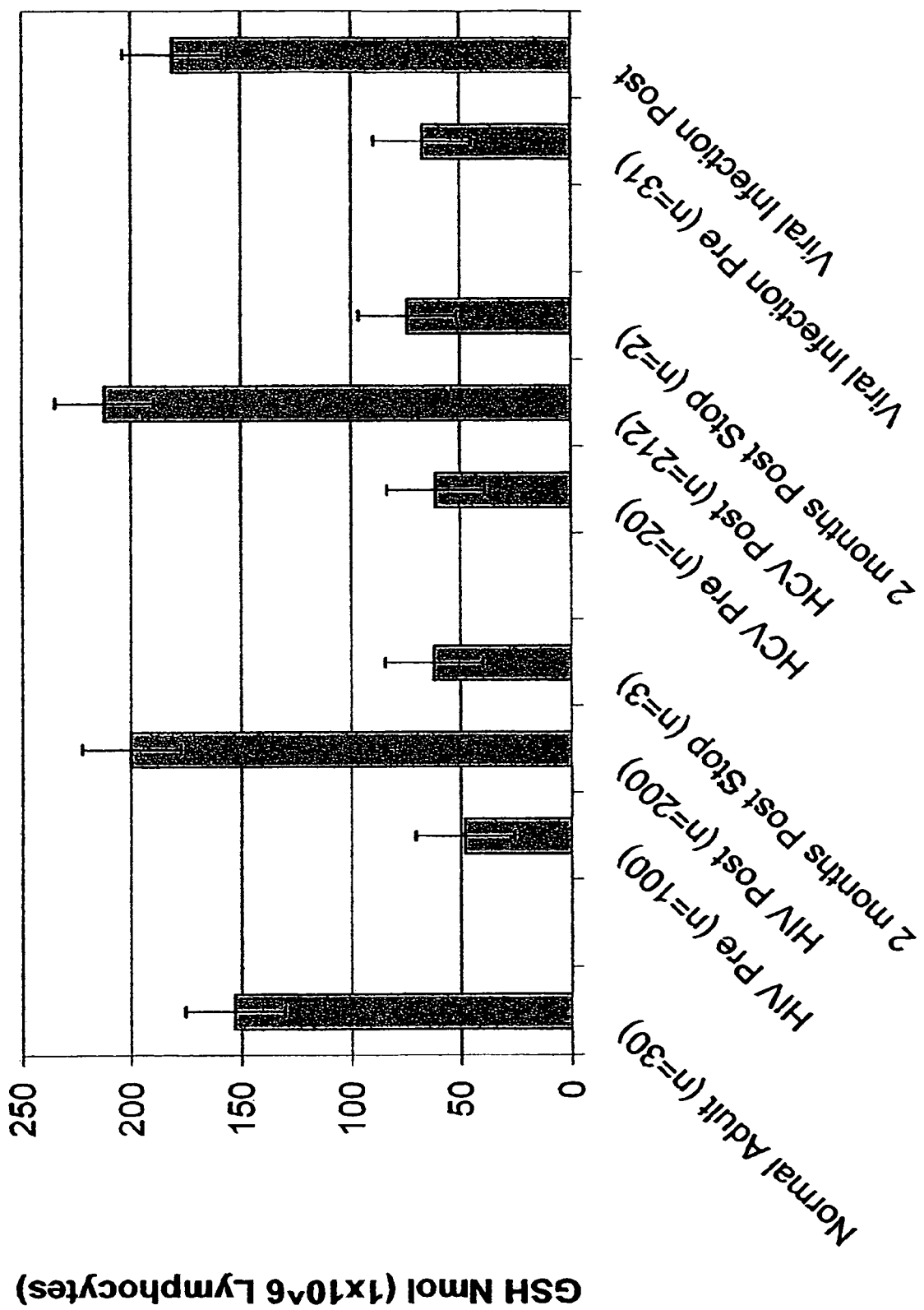
FIG. 4 is a graph illustrating the effects of administration of the compositions described in U.S. Pat. No. 6,262,019, the contents of which are hereby incorporated by reference, on glutathione (GSH) levels in lymphocytes of human patients infected with HIV, HCV, or other viruses.

The compositions described in U.S. Pat. No. 6,262,019 elevate glutathione (GSH) levels and can be beneficially administered to patients infected with various viral infections, such as HIV, HCV (hepatitis C) or other viral infections. This is illustrated in FIG. 4 which provides a graph illustrating the effects of administration of the compositions described in U.S. Pat. No. 6,262,019 on GSH levels in lymphocytes of human patients. It can be seen that the level of GSH is greatly reduced in patients infected with HIV, HCV, or other viruses, and that treatment with the compositions of U.S. Pat. No. 6,262,019 restores GSH levels to normal or even greater than normal levels. It can also be seen that two months after treatment is stopped, GSH levels decrease to around pre-treatment levels.

The compositions of the present invention are beneficially administered in combination with the compositions described in U.S. Pat. No. 6,262,019 to patients infected with avian influenza, including the H5N1 strain of avian influenza, in order to treat the infection. It is understood that the proportions and ingredients may be adjusted depending on various factors including the stage of illness as well as the subject's tolerances of the individual components.

Example 8

It is believed that the antiviral and other effects of the compositions of the present invention are mediated, at least in part, by the binding of quercetin to CD4+ T cells. This hypothesis was tested in an experiment using PBMCs isolated from patients who had been treated with a composition of the present invention referred to as "PBS119". The PBS 119 composition used comprised verapamil 120 mgs, dilantin 200 mgs, chloroquine 100 mgs, and quercetin 1200 mgs. The patients also received a multivitamin component which is useful in decreasing the metabolic consequences of the PBS119 components. The multivitamin component has several beneficial effects for example increasing levels of Glutathione, DHEA, selenium, zinc, vitamins C, A and beta carotene.

Samples consisting of $1 \times 10^6$ PMBCs were separated by ficoll-hypaque (Sigma-Aldrich) density gradient separation (specific gravity 1.078). Cells were then suspended in 1 ml of phosphate buffered saline (PBS), either with or without addition of 1% Nonidet P40 (Sigma Aldrich). The cells were incubated for 30 minutes in a humidified 37 degree 5% $CO_2$ atmosphere. Nonidet P40 is a mild non ionic detergent, treatment with which removes non-specifically bound substances from the cell surface. The cells were then washed three times in PBS and the cell pellet was suspended in 100 lambda of anti-CD3/CD4 (Becton Dickenson). The cells were incubated in the presence of the antibodies for 30 minutes at room temperature and then subjected to flow cytometric analysis. CD16/CD45 labelling was used to gate(separate) lymphocytes. Appropriate mouse IGG subclass controls (Becton Dickenson) were employed.

Figure 5:
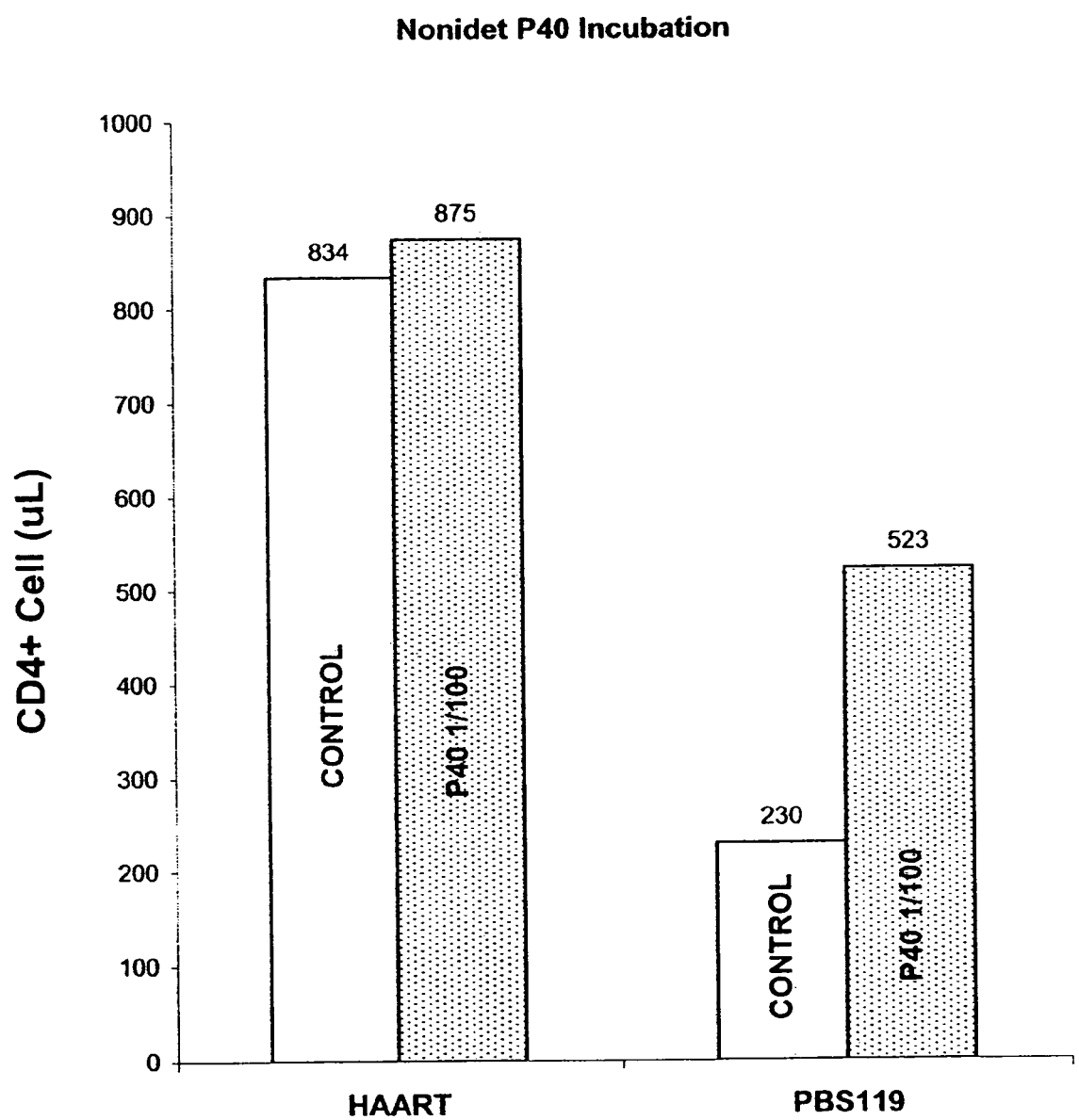
FIG. 5 is a graph illustrating the numbers of CD4+ cells detected using flow cytomerty in cells that were labeled with anti-CD4 antibodies in samples from patients that had been treated with either HAART or PBS119. Treatment of the peripheral blood mononuclear cells (PBMCs) with Nonidet P40 was used to remove non-specifically bound PBS119 prior to incubation with anti-CD4 antibodies.

The results of data from a single PBS119 treated patient is illustrated in FIG. 5. It can be seen that a higher number of CD4+ cells were detected in the cell sample that had been treated with 1% Nonidet P40. This is believed to be because the PBS-119, in particular the quercetin component of PBS119, has been "washed-off" by the NP-40 thereby allowing the anti-CD4 antibody to bind to the cells. Conversely, it can be seen that a lower number of CD4+ cells were detected in the cell sample that was not treated with 1% NP40, the reason being that the PBS119, in particular the quercetin component of the PBS-119, is non-specifically bound to the cells thereby preventing the anti-CD4 antibody from binding. By way of a control, FIG. 5 also shows data from a single HAART-treated patient, and illustrates that there is no significant difference in the binding of anti-CD4 to cells that have been treated with Nonidet P40, presumably because there was no substance non-specifically bound to these cells that blocked anti-CD4 binding. The graph depicted in FIG. 5 represents one of a number of comparative experiments. Combining data from multiple patients was not possible due to the wide variations in initial CD4 cell counts.

It is believed that the antiviral activity of the compositions of the present invention comprising quercetin against other viruses, such as the avian influenza virus, may be mediated, at least in part, by binding of quercetin to the surface of other cell types in addition to T cells. For example, it is believed that the compositions of the present invention comprising quercetin also bind to cells such as epithelial cells—a cell type infected by the avian influenza virus. It is also believed that the compositions of the present invention comprising quercetin may bind to the surface of other cell types. For example, it is believed that the compositions of the present invention comprising quercetin may bind to/block hepatocytes and thereby block or inhibit binding of the Hepatitis C virus.

It should be noted that compositions according to the present invention may vary from the exact amounts used to treat the patients in this example. For example, compositions can be used in which the amount of verapamil is in the range 80-240 mgs, the amount of dilantin is in the range 100-300 mgs, the amount of chloroquine is in the range 100-250 mg, and the amount of quercetin is in the range 1200-2400 mgs. Other amounts of these components may also be used. In addition, other suitable calcium channel blockers can be used in the place of verapamil, other suitable anticonvulsants can be used in the place of dilantin, other suitable quinolines can be used in the place of chloroquine, and quercetin derivatives may be used in the place of quercetin. It is understood that the exact proportions and ingredients may be adjusted depending on various factors including the stage of illness as well as the subject's tolerances of the individual components.

Having thus described in detail preferred embodiments of the present invention, it is to be understood that the invention defined by the appended claims is not to be limited by particular details set forth in the above description, as many apparent variations thereof are possible without departing from the spirit or scope the invention.

The invention claimed is:

1. A method of reducing the activity of a single stranded RNA virus in a virus-infected subject wherein the single stranded RNA virus is selected from the group comprising HIV and an avian influenza virus, comprising administering to the subject a therapeutically effective amount of a composition comprising quercetin or a derivative thereof, at least one calcium channel blocker component, an anticonvulsant component, a quinoline or a derivative thereof, and a multivitamin component, in a therapeutically effective amount to reduce viral activity in the subject.

2. The method according to claim 1 wherein the avian influenza virus is an H5N1 of avian influenza virus.

3. A method of reducing the induction of a cytokine storm, which results from infection with the H5N1 avian influenza virus, in a subject comprising administering to the subject a therapeutically effective amount of a composition comprising quercetin or a derivative thereof, at least one calcium channel blocker component, an anticonvulsant component, a quinoline or a derivative thereof, and a multivitamin component, in sufficient amounts to reduce the induction of the cytokine storm.

4. The method according to claim 1 wherein the anticonvulsant is dilantin.

* * * * *